United States Patent
Kleinbaum et al.

(10) Patent No.: US 12,054,713 B2
(45) Date of Patent: Aug. 6, 2024

(54) ROTATIONALLY SEQUESTERED TRANSLATORS

(71) Applicant: Emerald Therapeutics, Inc., South San Francisco, CA (US)

(72) Inventors: Daniel J. Kleinbaum, Redwood City, CA (US); Brian M. Frezza, Redwood City, CA (US); Brad Bond, Palo Alto, CA (US); Jonathan Leung, Sunnyvale, CA (US); George W. Fraser, Mountain View, CA (US)

(73) Assignee: Emerald Therapeutics, Inc., South San Francisco, CA (US)

( * ) Notice: Subject to any disclaimer, the term of this patent is extended or adjusted under 35 U.S.C. 154(b) by 903 days.

(21) Appl. No.: 17/107,699

(22) Filed: Nov. 30, 2020

(65) Prior Publication Data

US 2021/0102207 A1 Apr. 8, 2021

Related U.S. Application Data

(60) Continuation of application No. 16/664,713, filed on Oct. 25, 2019, now Pat. No. 10,883,106, which is a continuation of application No. 15/470,754, filed on Mar. 27, 2017, now Pat. No. 10,479,994, which is a division of application No. 14/721,398, filed on May 26, 2015, now Pat. No. 9,624,495, which is a division of application No. 13/801,762, filed on Mar. 13, 2013, now Pat. No. 9,068,218.

(60) Provisional application No. 61/754,339, filed on Jan. 18, 2013.

(51) Int. Cl.
| | | |
|---|---|---|
| *C07H 21/04* | (2006.01) | |
| *B82Y 10/00* | (2011.01) | |
| *C12N 15/11* | (2006.01) | |
| *C12N 15/113* | (2010.01) | |
| *C12Q 1/68* | (2018.01) | |
| *G06N 3/00* | (2023.01) | |
| *G06N 3/123* | (2023.01) | |

(52) U.S. Cl.
CPC ............ *C12N 15/113* (2013.01); *B82Y 10/00* (2013.01); *C07H 21/04* (2013.01); *C12N 15/11* (2013.01); *C12Q 1/68* (2013.01); *G06N 3/002* (2013.01); *G06N 3/123* (2013.01); *C12N 2310/322* (2013.01); *C12N 2310/334* (2013.01)

(58) Field of Classification Search
None
See application file for complete search history.

(56) References Cited

U.S. PATENT DOCUMENTS

| | | |
|---|---|---|
| 6,238,927 B1 | 5/2001 | Abrams et al. |
| 7,501,253 B2 | 3/2009 | Pourmand et al. |
| 7,538,202 B2 | 5/2009 | Zhang et al. |
| 9,068,218 B2 | 6/2015 | Kleinbaum et al. |
| 9,624,495 B2 | 4/2017 | Kleinbaum et al. |
| 10,479,994 B2 | 11/2019 | Kleinbaum et al. |
| 2002/0119458 A1 | 8/2002 | Suyama et al. |
| 2003/0152924 A1 | 8/2003 | Ullman et al. |
| 2005/0075792 A1 | 4/2005 | Shapiro et al. |
| 2005/0112065 A1 | 5/2005 | Drummond et al. |
| 2007/0072215 A1 | 3/2007 | Seelig et al. |
| 2009/0170719 A1 | 7/2009 | Kazakov et al. |
| 2009/0191546 A1 | 7/2009 | Zhang et al. |
| 2011/0294687 A1 | 12/2011 | Kleinbaum |
| 2011/0306758 A1 | 12/2011 | Zhang |

FOREIGN PATENT DOCUMENTS

| | | |
|---|---|---|
| WO | WO-2008/097929 | 8/2008 |
| WO | WO-2008/141279 | 11/2008 |
| WO | WO-2012/151328 | 11/2012 |

OTHER PUBLICATIONS

Allawi et al., "Thermodynamics and NMR of Internal G-T Mismatches in DNA." Biochemistry vol. 36, (1997):10581-10594.
Anonymous, "DNA nanotechnology", Wikipeida, the free encyclopedia, 2012, https://en.wikipedia.org/wiki/DNA_nanotechnology?oldid=527955533, pp. 1-14.
Beaucage, S. L.; Uyer, R. P., Advances in the Synthesis of Oligonucleotides by the Phosphoramidite Approach, Tetrahedron, 1992, 48, 2223-2311.
Beck et al., "Solid Phase Synthesis of PNA Oligomers," Methods In Molecular Biology, vol. 208, pp. 29-41 (2009) Abstract.
Biswas et al., "Branch Migration Through DNA Sequence Heterology" J. Mol. Biol., (1998) 279, 795-806.
Braasch et al., "Locked nucleic acid (LNA): fine-tuning the recognition of DNA and RNA," Chemistry & Biology, 8 (2001) 1-7.
Brown et al., "A Brief History of Oligonucleotide Synthesis", Methods in Molecular Biology, pp. 1-17 (1993).
Corradini et al., "Control of helical handedness in DNA and PNA nanostructures," Methods in Molecular Biology, 749:79-92 (2011).
Doktycz et al., "Nucleic Acids: Thermal Stability and Denaturation," Encyclopedia of Life Sciences, pp. 1-18, John Wiley & Sons Ltd, Chichester. http://www.els.net [doi: 10.1038/npg.els.0003123] (Oct. 2002).
Dragulescu-Andrasi et al., "A simple gamma-backbone modification preorganizes peptide nucleic acid into a helical structure", Journal of the American Chemical Society, 2006, vol. 128, pp. 10258-10267.
Dragulescu-Andrasi et al., "Cell-permeable GPNA with appropriate backbone stereochemistry and spacing binds sequence-specifically to RNA," Chem. Commun., 2005, pp. 244-246.
Duose et al., "Configuring robust DNA strand displacement reactions for in situ molecular analyses", Nucleic Acids Research, vol. 40, No. 7, pp. 3289-3298 (2012).

(Continued)

*Primary Examiner* — Amanda Haney
(74) *Attorney, Agent, or Firm* — Sheppard Mullin Richter & Hampton LLP

(57) ABSTRACT

Provided are nucleic acid translators capable of carrying out logic operations with improved efficiency, maximized output and reduced off-target effects, in particular in a biological system. Methods of using these translators to transduce signal are also provided.

5 Claims, 32 Drawing Sheets

(56) References Cited

OTHER PUBLICATIONS

Extended European search report for European Application No. 14740468.5, dated Nov. 15, 2016. (15 pages).

Freier et al., "The ups and downs of nucleic acid duplex stability: structure-stability studies on chemically-modified DNA:RNA duplexes", Nucleic Acids Research, 1997, vol. 25, No. 22,, pp. 4429-4443.

Frezza et al., "Modular Multi-Level Circuits from Immobilized DNA-Based Logic Gates", J. Am. Chem. Soc., 2007, 129, pp. 14875-14879.

International Search Report and Written Opinion for International Application No. PCT/US2014/011782, dated May 22, 2014.

International Preliminary Report on Patentability for International Application No. PCT/US2014/011782, dated Jul. 21, 2015. (5 pages).

Iyer et al., "Oligonucleotide Synthesis", Comprehensive Natural Products Chemistry vol. 7 (DNA and Aspects of Molecular Biology), 1999, pp. 105-152.

Kahan et al., "Towards molecular computers that operate in a biological environment", Science Direct Physica D 237, (2008) 1165-1172.

Krane et al., "Time for DNA Disclosure", Science, vol. 326, Dec. 18, 2009, 1631-1633.

Kutyavin et al., "Oligonucleotides Containing 2-Aminoadenine and 2-Thiothymine Act as Selectively Binding Complementary Agents," Biochemistry (1996) 35:11170-11176.

Lakin et al., "Design and Analysis of DNA Strand Displacement Devices Using Probabilistic Model Checking", Journal of The Royal Society Interface, 9(72): 1470-1485 (especially pp. 1481-1484) (2012).

Laplanche et al., "Phosphorothioate-Modified Oligodeoxyribonucleotides. III. NMR and UV Spectroscopic Studies of the Rp-Rp, Sp-Sp and Rp-Sp, Duplexes (d(GGSAATTCC))2, Derive from Diastereomeric O-Ethyl Phosphorothioates", Nucleic Acids Research, 14(22):9081-9093 (1986).

Latimer et al., "Synthetic repeating sequence DNAs containing phosphorothioates: nuclease sensitivity and triplex formation," Nucleic Acids Res. 17(4):1549-1561 (1989).

Lee et al., "Chitosan: a novel platform in proton-driven DNA strand rearrangement actuation," Mol. BioSyst. (2009) 5:391-396.

Li et al., "A new class of homogeneous nucleic acid probes based on specific displacement hybridization." Nucleic Acids Research, vol. 30, No. 2, pp. E5.1-E5.9 (2002).

Lusvarghi et al., "Loop and backbone modifications of peptide nucleic acid improve G-Quadruplex binding selectivity", JACS, 131, 18415-18424, (2009).

Ma et al., "3-Arm Nucleic Acid Junctions are Flexible", Nucleic Acids Research, 14:9745-9753 (1986).

Maugh II, "Wolf & Lamb Chemistry, Many useful reactions difficult to perform by conventional means can be carried out easily with polymeric reagents", Science, vol. 217, Aug. 20, 1982, pp. 719-720.

Nielsen et al., "An Introduction to Peptide Nucleic Acid", Current Issues Molec. Biol. (1999), 1(2):89-104.

Nishikawa et al., "DNA computation simulator based on abstract bases", Soft Computing 5:25-38 (2001).

Ortega et al., "Binding Affinities of Oligonucleotides and PNAs Containing Phenoxazine and G-Clamp Cytosine Analogues are Unusually Sequence Dependent", Organic Letters, 2007, vol. 9, No. 22, 4503-4506.

Panyutin et al., "Formation of a Single Base Mismatch Impedes Spontaneous DNA Branch Migration", J. Mol. Biol., 230:413-424 (1993).

Panyutin et al., "The kinetics of spontaneous DNA branch migration", Proceedings of the National Academy of Sciences of USA, vol. 91, Mar. 1994, pp. 2021-2025.

Partial supplementary European search report for European Application No. 14740468.5, dated Aug. 12, 2016. (10 pages).

Picuri et al., "Universal Translators for Nucleic Acid Diagnosis", J. Am. Chem. Soc. (2009) 131:9368-9377.

Sager et al., "Designing nucleotide sequences for computation: A survey of constraints", DNA11, LNCS 3892: 275-289, (2006).

Sahu et al., "Synthesis of Conformationally Preorganized and Cell Permeable Guanidine-Based Peptide Nucleic Acids (GPNAs)", J. Org. Chem. 2009, 74, 1509-1516.

Seelig et al., "Enzyme-Free Nucleic Acid Logic Circuits", Science, vol. 314, Dec. 8, 2006, pp. 1585-1588.

Seeman et al., "DNA Branched Junctions", Annu. Rev. Biophys. Biomol. Struct. 1994. 23:53-86.

Seeman et al., "Nanotechnology and the double helix", Scientific American, 2004, vol. 290, No. 6, pp. 64-75.

Summerton et al., "Morpholino Antisense Oligomers: Design, Preparation, and Properties", Antisense & Nucleic Acid Drug Development 7:187-195 (1997).

Tajima et al., "Direct Oxidative Cyanation Based on the Concept of Site Isolation", J. Am. Chem. Soc. 2008, 130, 10496-10497.

Uhlmann et al., "Synthesis and Properties of PNA/DNA Chimeras", Angew. Chem. Ed. Engl. 35(22):2632-2635 (1996).

Voelcker et al., "Sequence-Addressable DNA Logic", Small 2008, 4, No. 4, pp. 427-431.

Voit et al., "Sequential One-Pot Reactions Using the Concept of Site Isolation", Angewandte Chemical International Edition (2006) 45:4238-4240.

Yashin et al., "Networking Particles over Distance Using Oligonucleotide-Based Devices", J. Am. Chem. Soc. (2007) 129:15581-15584.

Zhang et al., "Control of DNA Strand Displacement Kinetics Using Toehold Exchange", J. Am. Chem. Soc. (2009) 131:17303-17314.

Zhang et al., "Dynamic DNA nanotechnology using strand-displacement reactions", Nature Chemistry, vol. 3, No. 2, pp. 103-113 (2011).

Zhang et al., "Engineering entropy-driven reactions and networks catalyzed by DNA", Science, vol. 318, Nov. 2007, pp. 1121-1125.

Zhou et al., "Novel Binding and Efficient Cellular Uptake of Guanidine-Based Peptide Nucleic Acids (Gpna)", J. Am. Chem. Soc., 2003, 125:23, 6878-6879.

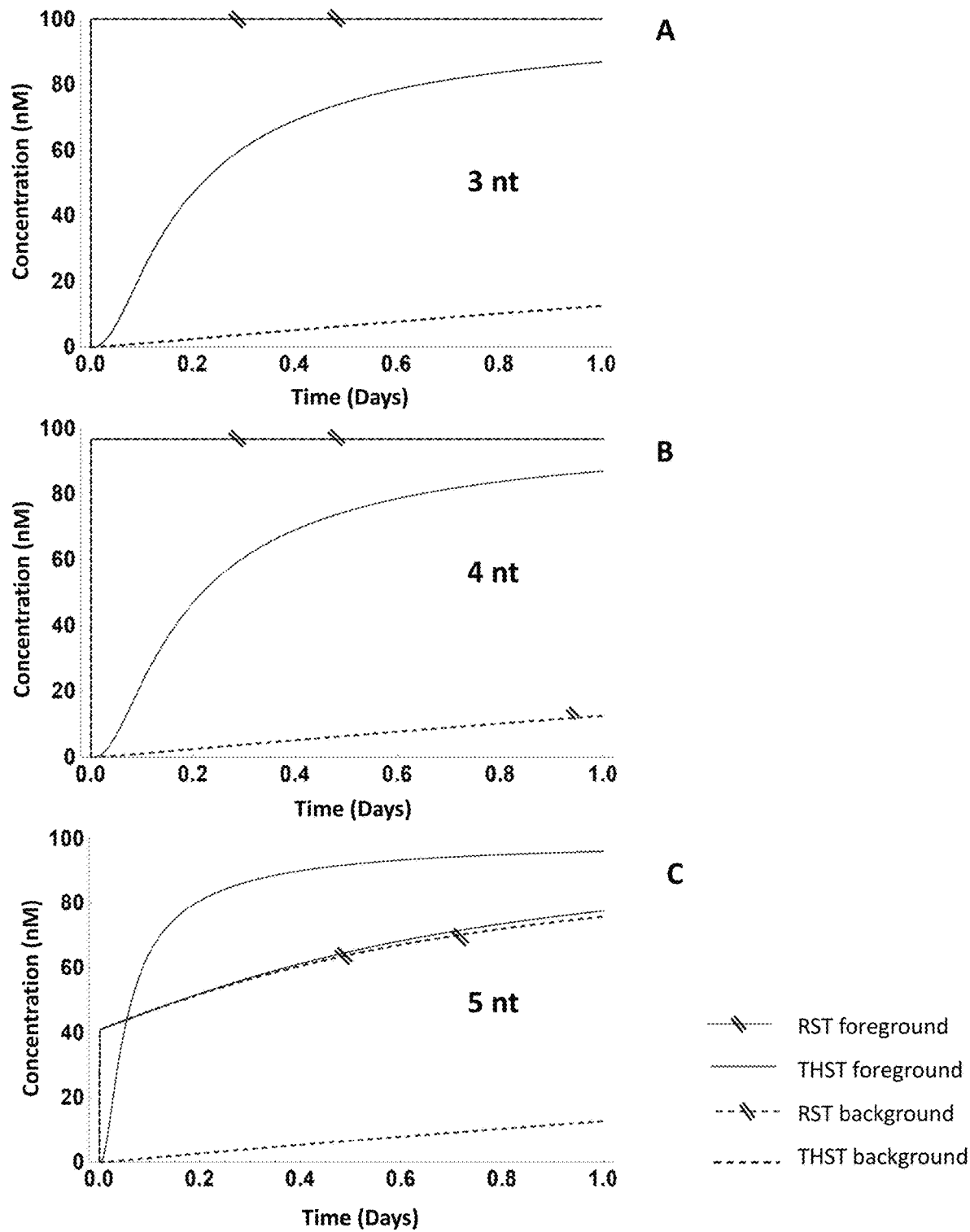
FIG. 17A-C

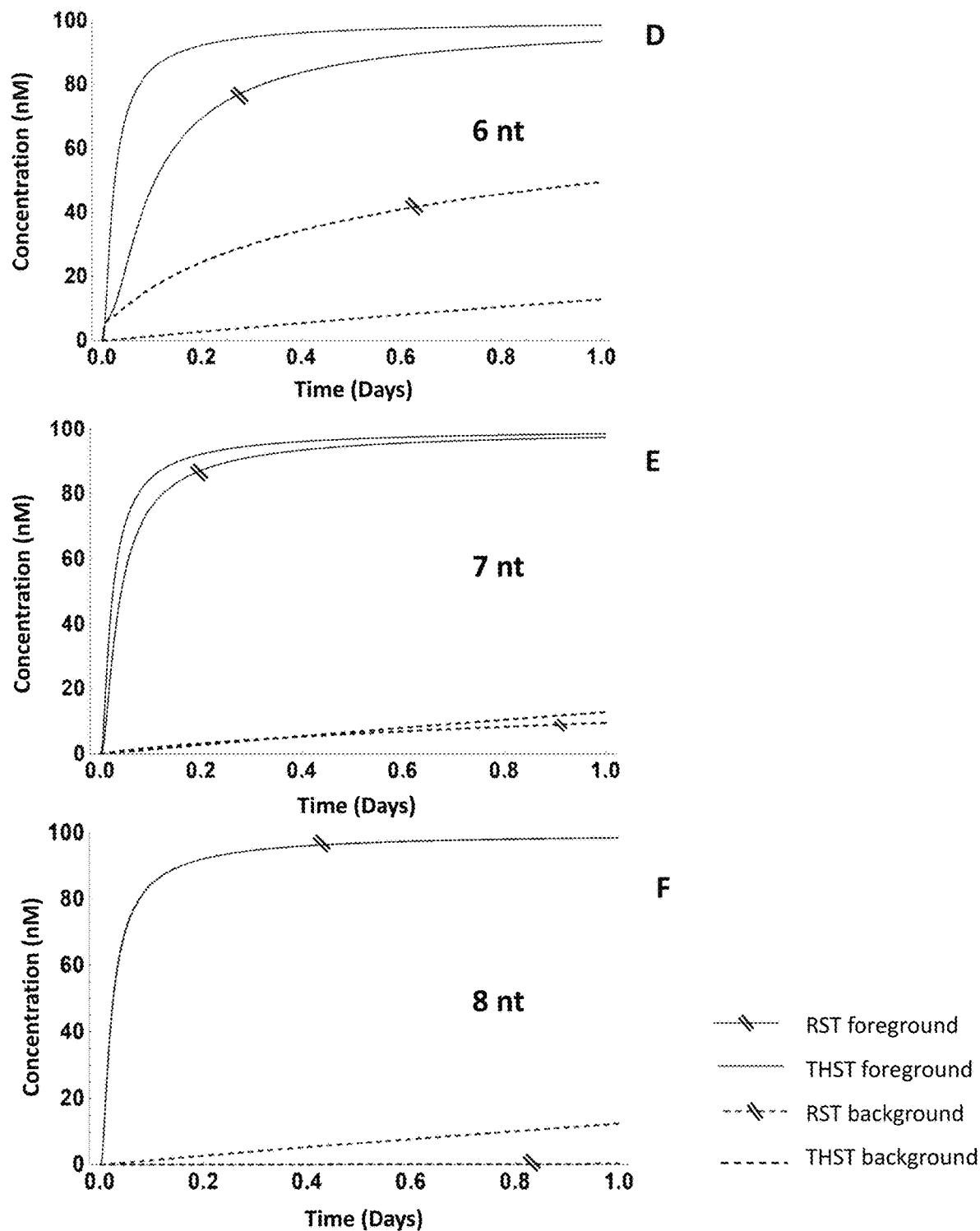
FIG. 17D-F

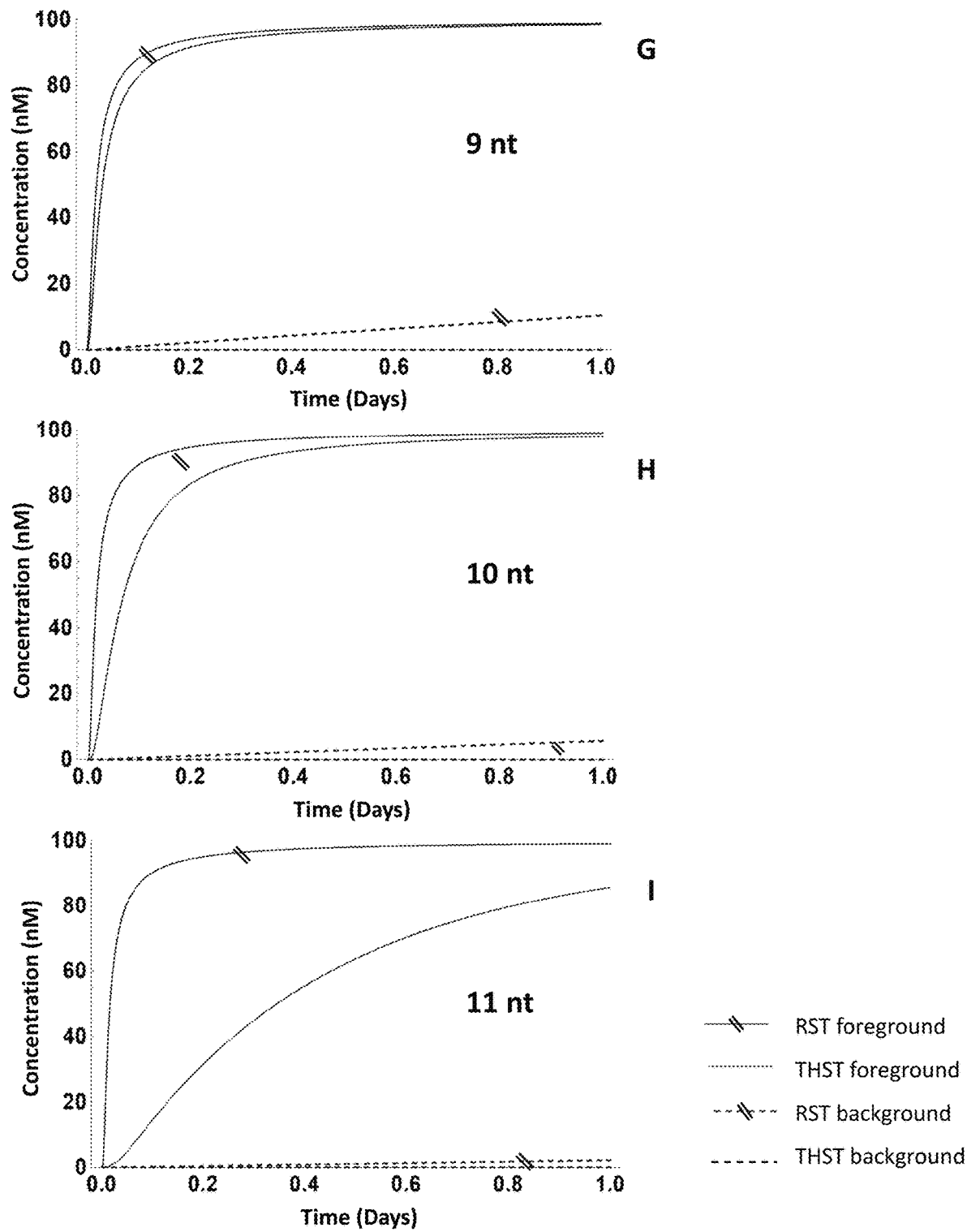
FIG. 17G-I

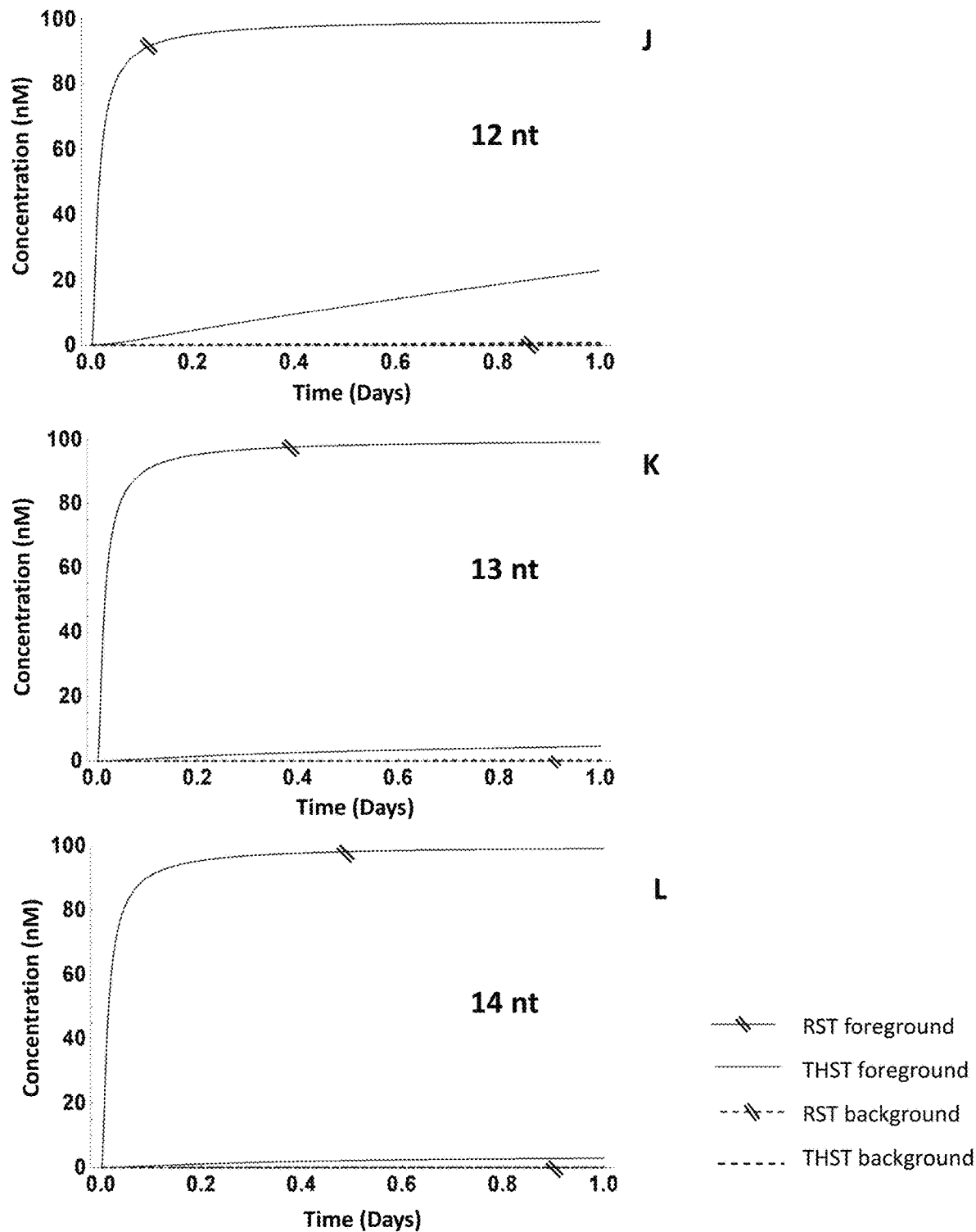
FIG. 17J-L

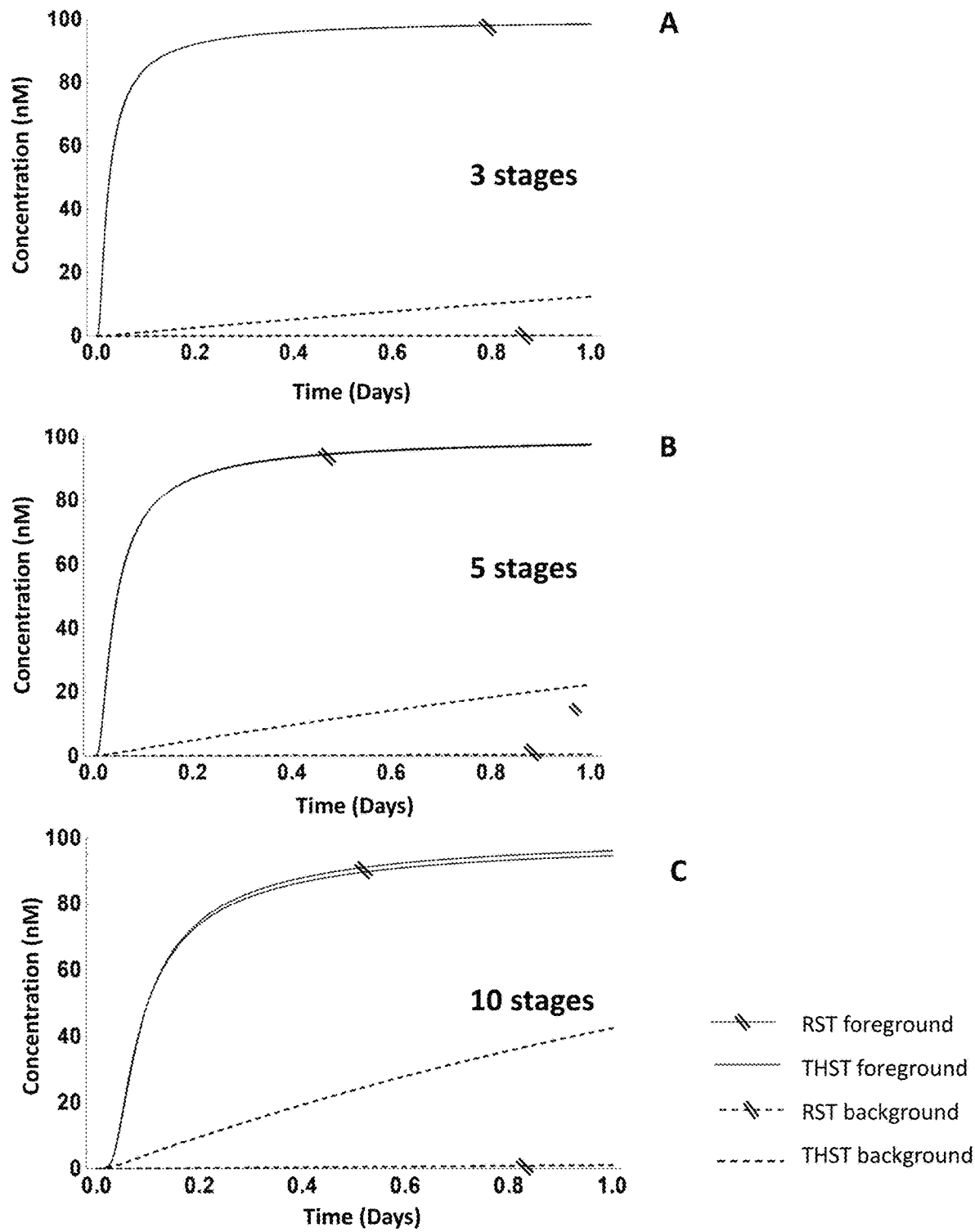
FIG. 18A-C

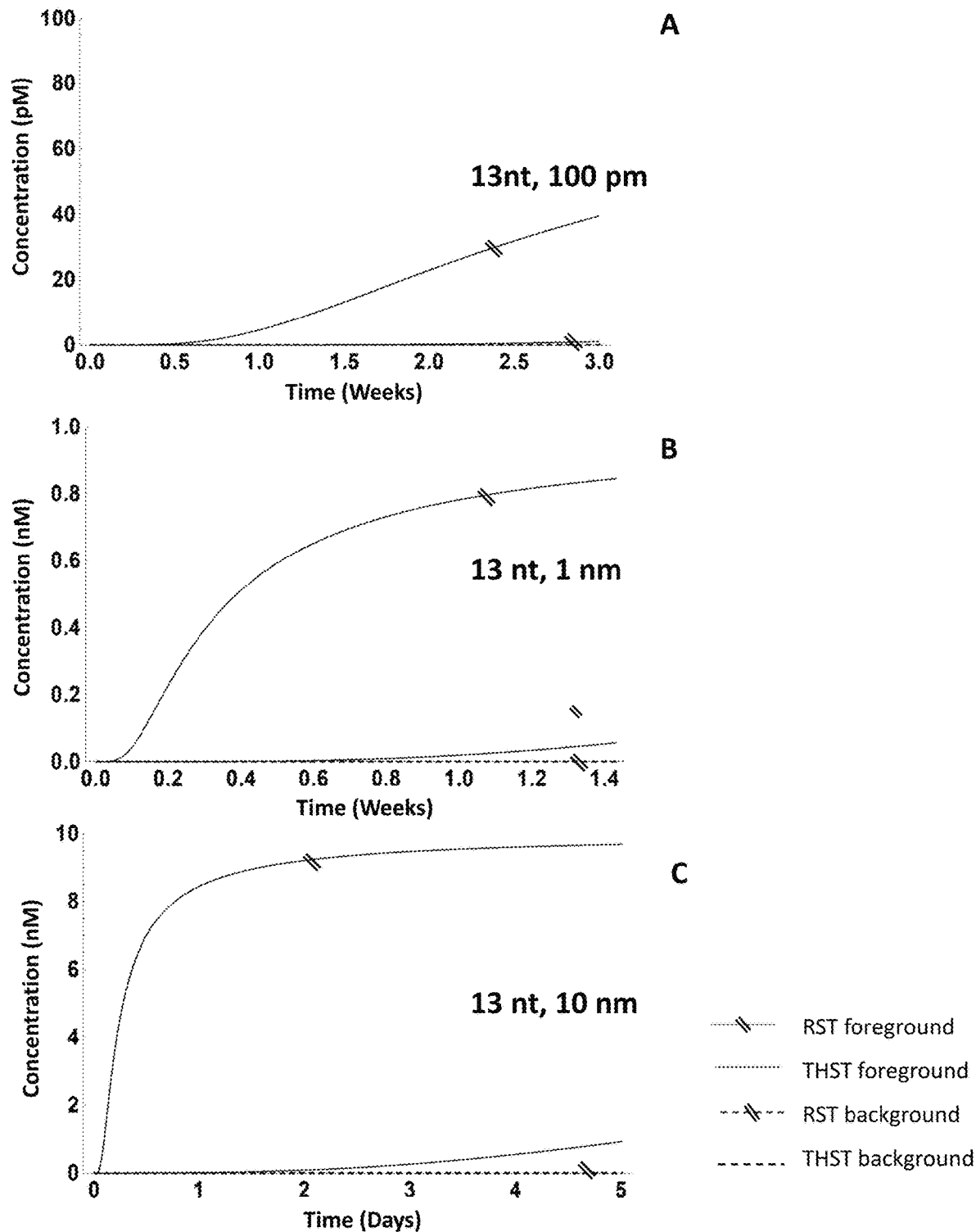
FIG. 19A-C

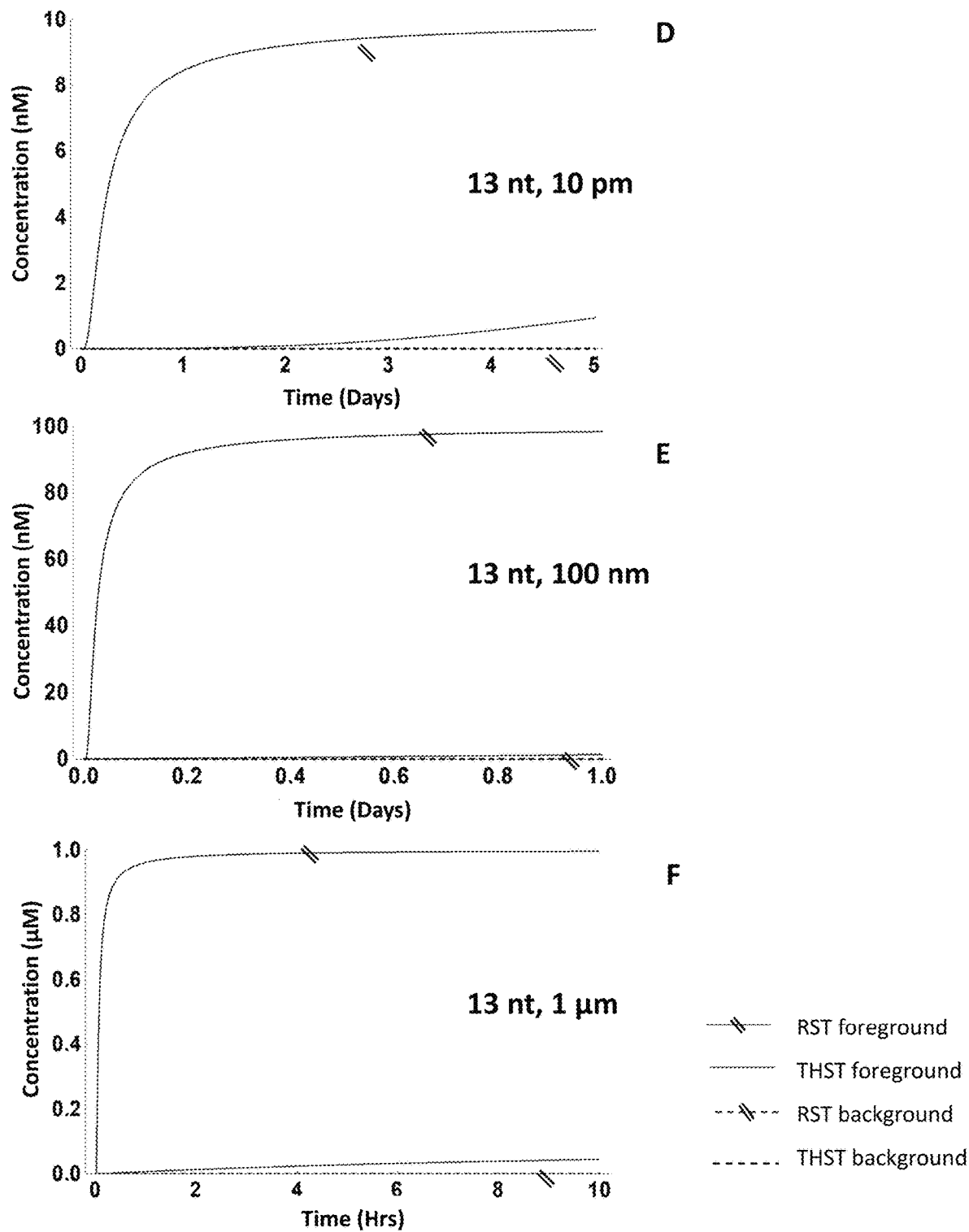
FIG. 19D-F

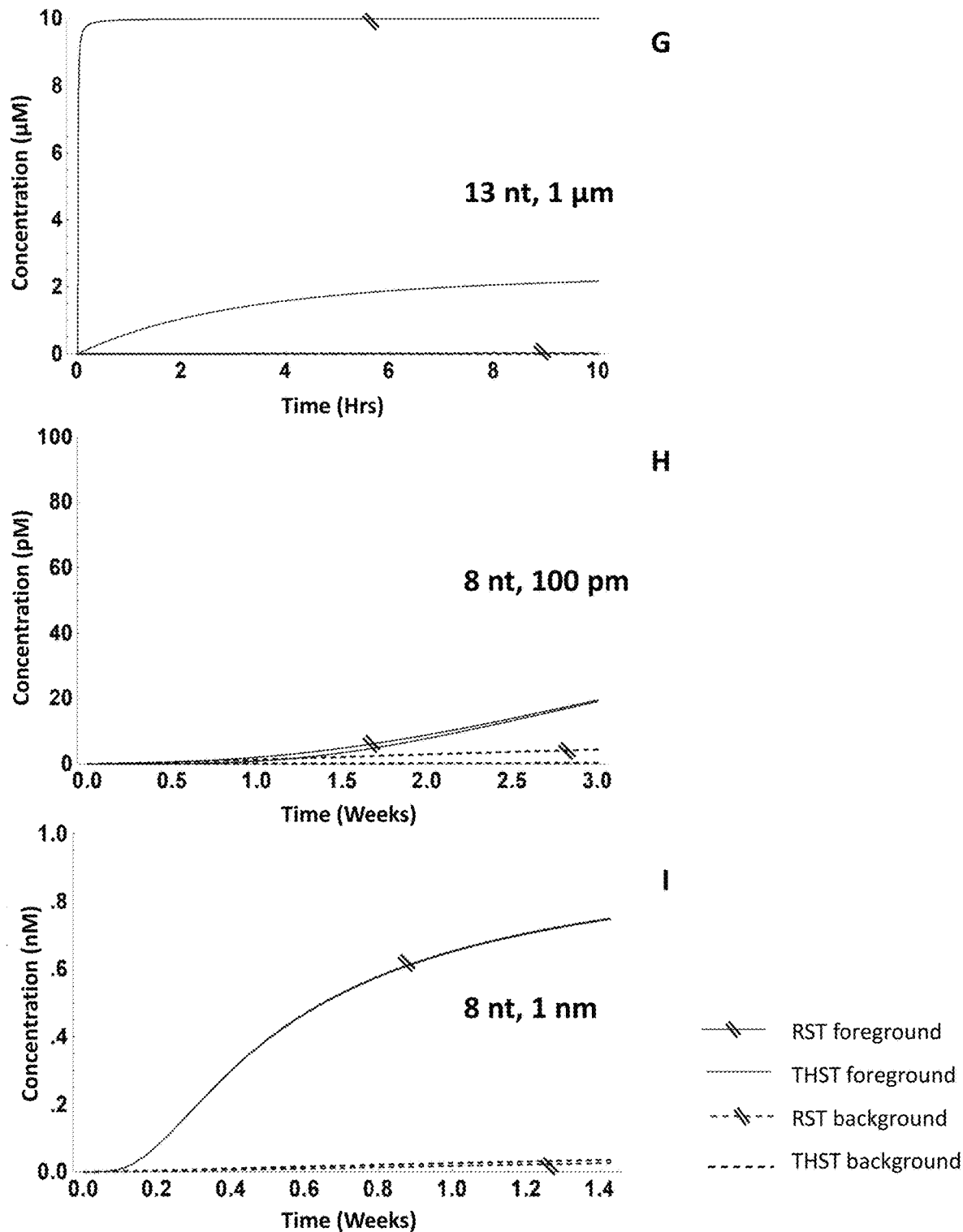
FIG. 19G-I

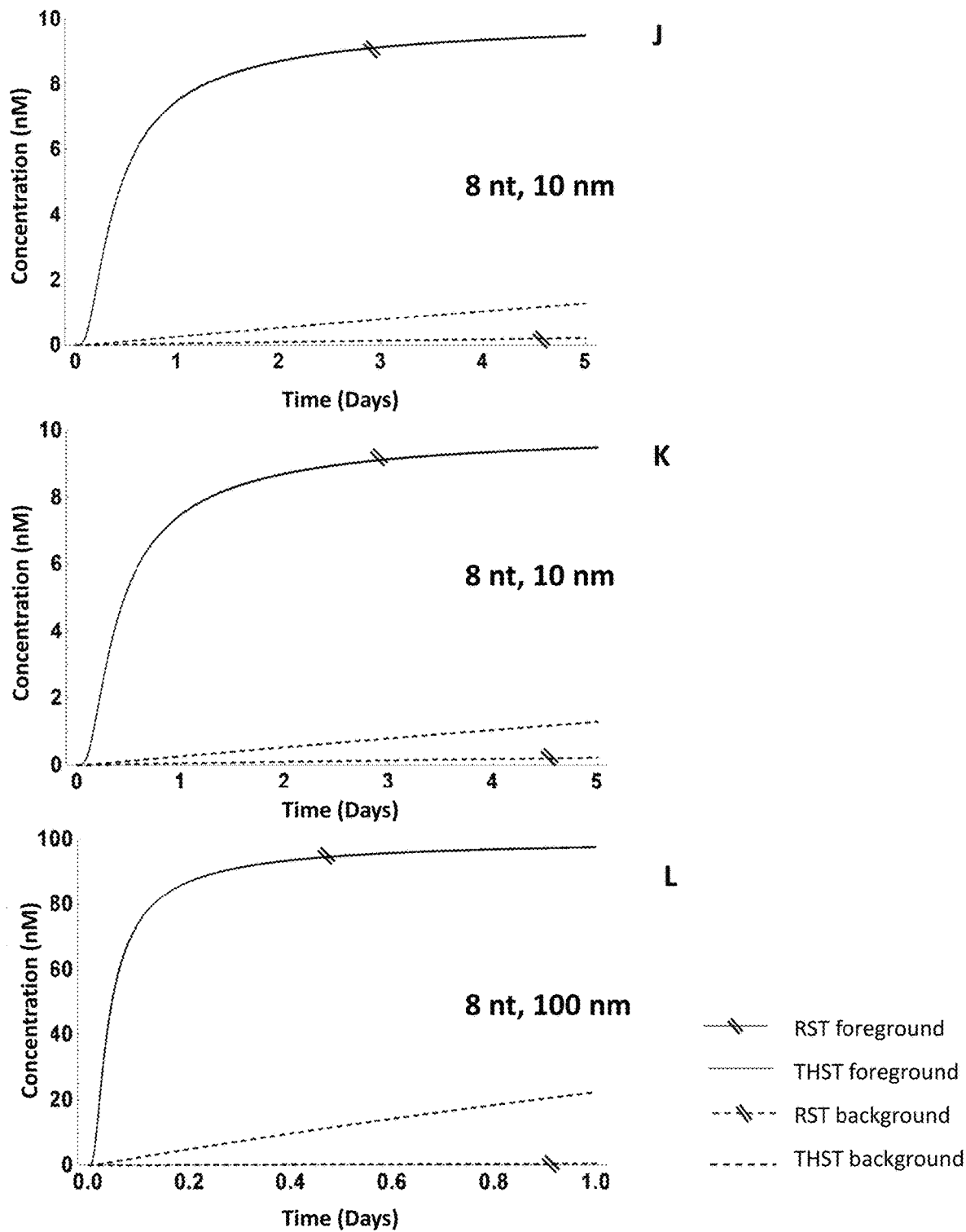
FIG. 19J-L

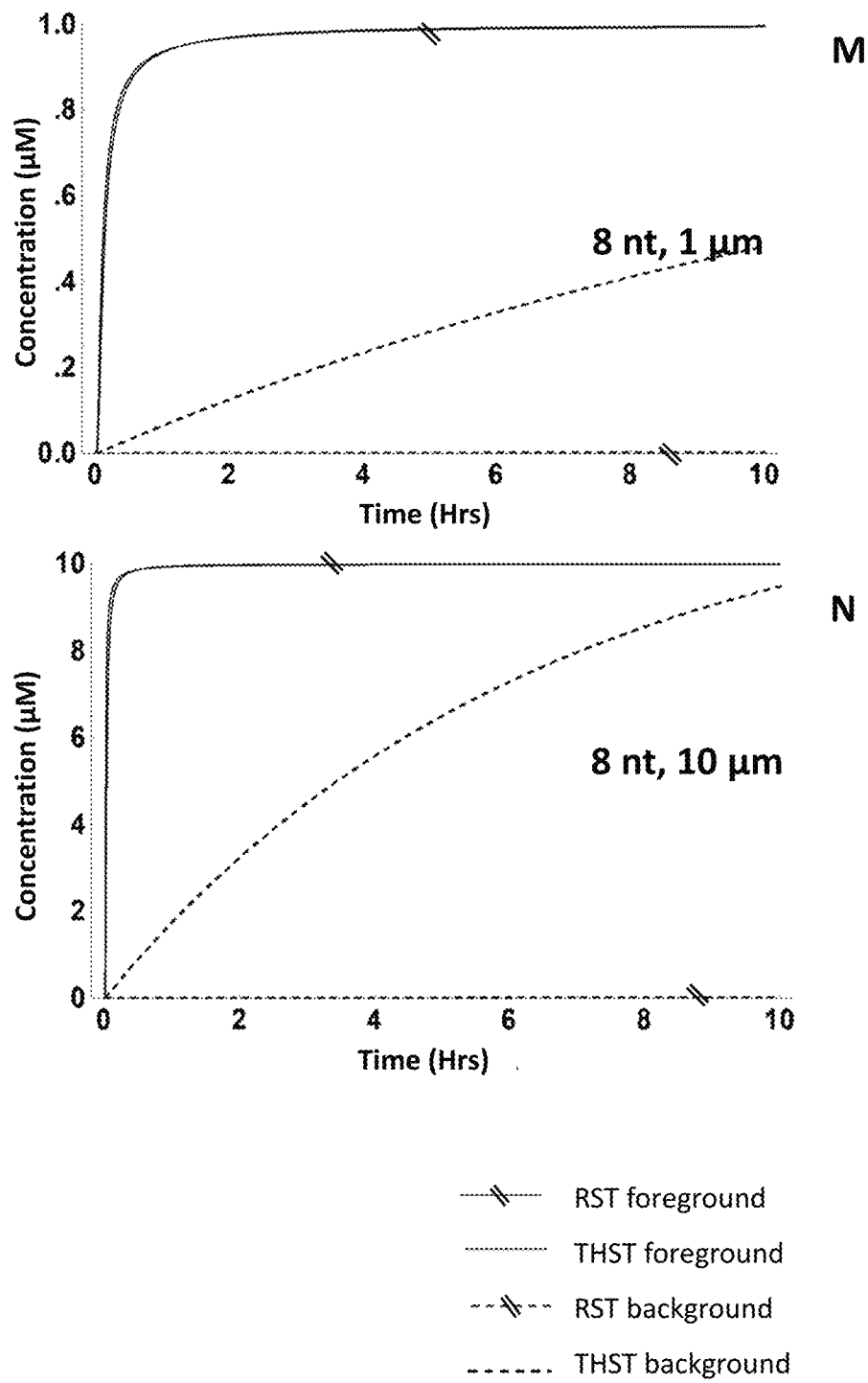
FIG. 19M-N

ROTATIONALLY SEQUESTERED TRANSLATORS

CROSS-REFERENCE TO RELATED APPLICATIONS

This application is a continuation of U.S. application Ser. No. 16/664,713, filed Oct. 25, 2019, now U.S. Pat. No. 10,883,106, which is a continuation of U.S. application Ser. No. 15/470,754, filed Mar. 27, 2017, now U.S. Pat. No. 10,479,994, which is a divisional of U.S. application Ser. No. 14/721,398, filed May 26, 2015, now U.S. Pat. No. 9,624,495, which is a divisional of U.S. application Ser. No. 13/801,762, filed Mar. 13, 2013, now U.S. Pat. No. 9,068,218, which claims the benefit under 35 U.S.C. § 119(e) to U.S. Provisional Application No. 61/754,339, filed Jan. 18, 2013, the contents of each of which are incorporated here by reference in their entireties.

BACKGROUND

Producing nano-scale computers with molecules offers substantial potential, in part because such computers may be well-suited for solving certain computation problems. In particular, computers employing biomolecules can be compatible with biological environments, rendering them amenable for use in complex-disease diagnostics or even treatments.

The ability to translate one nucleic acid sequence into another in principle allows one to build logic gates and networks with nucleic acids. These gates and networks are driven by two events, hybridization and strand displacement, both of which generally are thermodynamically favorable, i.e., they involve a transition from a higher—to a lower-energy state. Thus, both events can occur spontaneously in a system.

Hybridization involves free, single-stranded stretches of nucleic acids. Accordingly, a nucleic-acid network may be regulated by the availability of these free strands.

A "sequestering event" allows certain sequences to be available conditionally to the rest of the network. Such events empower the construction of translators, which convert one single-stranded nucleic acid sequence into a different single-stranded nucleic acid sequence. These translators are the foundation on which can be built, with nucleic acids, basic logic operators such as AND, NOT, OR, NAND, NOR, XOR and XNOR. From these and other logic components, larger networks can be constructed that include components such as amplifiers. Accordingly, these translation events are important for information processing with nucleic acids and molecular computing.

SUMMARY

In accordance with one aspect of the present invention, provided is a composition comprising a first and a second nucleic acid complexes each comprising a first, a second, a third, and a fourth nucleic acid strands, each of the strands comprising, sequentially, a first, a second and a third fragments, wherein the nucleic strands are defined as B-X-D, $\overline{C}$-$\overline{X}$-$\overline{A}$, $\overline{D}$-$\overline{Y}$-E and F-Y-C for the first, second, third and fourth strands of the first complex, respectively, and $\overline{C}$-$\overline{Y}$-$\overline{T}$, E-Y-D, F-Z-G, $\overline{H}$-$\overline{Z}$-$\overline{E}$ for the first, second, third and fourth strands of the second complex, respectively, wherein each letter denotes a fragment and each string of letters connected by "-" denotes a strand, and wherein: each of the first and the second complexes comprises a first duplex region formed between the second fragments of the first and second strands (X::$\overline{X}$ and Y::$\overline{Y}$, in the first and second complexes, respectively), a second duplex region formed between the second fragments of the third and fourth strands (Y::$\overline{Y}$ and Z::$\overline{Z}$), a third duplex region formed between the third fragment of the first strand and the first fragment of the third strand (D::$\overline{D}$ and F::F), and a fourth duplex region formed between the first fragment of the second strand and the third fragment of the fourth strand ($\overline{C}$::C and E::$\overline{E}$), in each of the first and second complexes, the first fragment (B and $\overline{C}$, in the first and second complexes, respectively) of the first strand, the third fragment ($\overline{A}$ and D) of the second strand, the third fragment (E and G) of the third strand and the first fragment (F and $\overline{H}$) of the fourth strand are single-stranded; the third strand of the first complex ($\overline{D}$-$\overline{Y}$-E) has suitable sequence complementarity to the second strand of the second complex (E-Y-D) to allow binding therebetween under hybridizing conditions; and the fourth strand of the first complex (F-Y-C) has suitable sequence complementarity to the first strand of the second complex ($\overline{C}$-$\overline{Y}$-F) to allow binding therebetween under hybridizing conditions.

In one aspect, the composition further comprises a third nucleic acid complex comprising a first and a second nucleic acid strands, each of the strands comprising, sequentially, a first, a second and a third fragments, wherein the first and second strands are defined as E-Z-H and $\overline{G}$-$\overline{Z}$-$\overline{F}$ respectively, wherein the third nucleic acid complex comprises a duplex region formed between the second fragments of the first and second strands (Z::$\overline{Z}$) and the first fragment (E) of the first strand and the third fragment of the second strand ($\overline{F}$) are singled-stranded, and wherein:

the third strand of the second complex (F-Z-G) has suitable sequence complementarity to the second strand of the third complex ($\overline{G}$-$\overline{Z}$-$\overline{F}$) to allow binding therebetween under hybridizing conditions; and the fourth strand of the second complex ($\overline{H}$-$\overline{Z}$-$\overline{E}$) has suitable sequence complementarity to the first strand of the third complex (E-Z-H) to allow binding therebetween under hybridizing conditions.

In some aspects, the third fragment ($\overline{E}$) of the third strand of the first complex and the first fragment (E) of the first strand of the third complex have sequence complementarity but do not stably bind to each other under normal hybridizing conditions due to chemical modification to either or both of the fragments; and the first fragment (F) of the fourth strand of the first complex and the third fragment ($\overline{F}$) the first strand of the third complex have sequence complementarity but do not stably bind to each other under normal hybridizing conditions due to chemical modification to either or both of the fragments.

Chemical modifications suitable for practicing the present technology include, without limitation, replacing sugar-phosphodiester backbone of a nucleic acid fragment with a mini-PEG-conjugated, serine-derived gamma-PNA. In some aspects, the chemical modification comprises substituting a tricyclic cytosine analogue for the nitrogenous base of at least one nucleoside in a nucleic acid fragment. In one aspect, the chemical modification comprises introducing a heteroatom at the 2'-position of a sugar moiety in a nucleotide.

Illustrations of the complexes and their relationships can be found in FIG. 6A, where translator 102 corresponds to the first complex, translator 103 corresponds to the second complex, and translator 104 corresponds to the third complex. Likewise, FIGS. 10-13, 14A-D, and 15-16, also illustrate translators (nucleic acid complexes) within the scope of the present disclosure, including each individual translator and their combinations as translator sets (or in the form of a composition).

In one aspect, each fragment is from about 5 bases to about 50 bases long. In another aspect, each each fragment that is single-stranded is from about 5 bases to about 30 bases long.

It also is within the scope of the disclosure that each composition can further optionally comprise a pharmaceutically acceptable carrier. Some embodiments of the present disclosure, further, provide a cell comprising the composition or complex of the present disclosure.

Computer-implemented methods and non-transitory computer-readable media suitable for simulating, designing, recording, reporting, or analyzing certain aspects of the disclosed technology are also provided here.

BRIEF DESCRIPTION OF THE DRAWINGS

Provided as embodiments of this disclosure are drawings which illustrate by exemplification only, and not limitation, wherein:

FIG. 17A-M present the simulation results for both the Rotationally Sequestered Translator (RST) networks and the Toe-Hold Sequestered Translator (THST) networks, with respect to both foreground signal and background signal, for different sizes of the toe-holds, ranging from 3 nucleotides (nt) to 15 nt (as indicated). All simulations were conducted with 100 nM translators for 3 stages;

FIG. 18A-D show the simulation results for the RST and THST networks at different depths (i.e., number of involved transistors/stages, as indicated) of the networks. All simulations were conducted with an 8 nt toe-hold at 100 nm translator concentrations; and FIG. 19A-N present the simulation results with moderate sized networks (5 stages) for both long (13 nt) and short (8 nt) toe-holds and show how the networks' behavior changed with variation in in the indicated concentrations of the translators.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Solid-phase sequestering, toe-hold sequestering, and toe-hold exchange are among the various approaches that can be used in translating nucleic acid sequences to build logic operators and networks. Described in greater detail below, these three particular approaches are exemplified via geometries that utilize three-way, toe-hold-mediated branch migration reactions. Additional mechanisms are possible for branch migration reactions, including but not limited to four-way branch migration, four-way accelerated migration, and multi-strand complex migration.

Thus, while there are embodiments described below that employ three-way branch migration for illustration purposes, the present invention contemplates DNA logic gates and networks built to utilize other branch migration pathways. Conversely, the embodiments of the invention can be applied to any branch migration reaction.

Throughout this disclosure and in the accompanying figures, capital letters, e.g., A, B, C, X, Y, Z, optionally with subscripts or superscripts, are used to represent a stretch, also referred as a "fragment," of oligonucleotides of arbitrary length. The corresponding A', B', C', X', Y', Z' or interchangeably $\overline{A}$, $\overline{B}$, $\overline{C}$, $\overline{X}$, $\overline{Y}$, $\overline{Z}$ represent the respective reverse complement.

The terms "oligonucleotides," "polynucleotides" and "nucleic acids" are used here to encompass all forms of nucleic acid molecules. Without limitation, this category includes ribonucleic acids (RNA), deoxyribonucleic acid (DNA), peptide nucleic acids (PNA), and their derivatives, with and without modifications, respectively.

Solid-Phase Sequestering

Solid-phase sequestering entails physical separation of the relevant sequences/strands in space by means of beads, nanoparticles, or surfaces. This approach employs principles of site isolation, which have found extensive use in organic chemistry. The timing of these displacement events in solid-phase sequestered geometries can be controlled by regulating whether the necessary strands are in the solution phase or in the solid phase of the system.

Figure 1A:
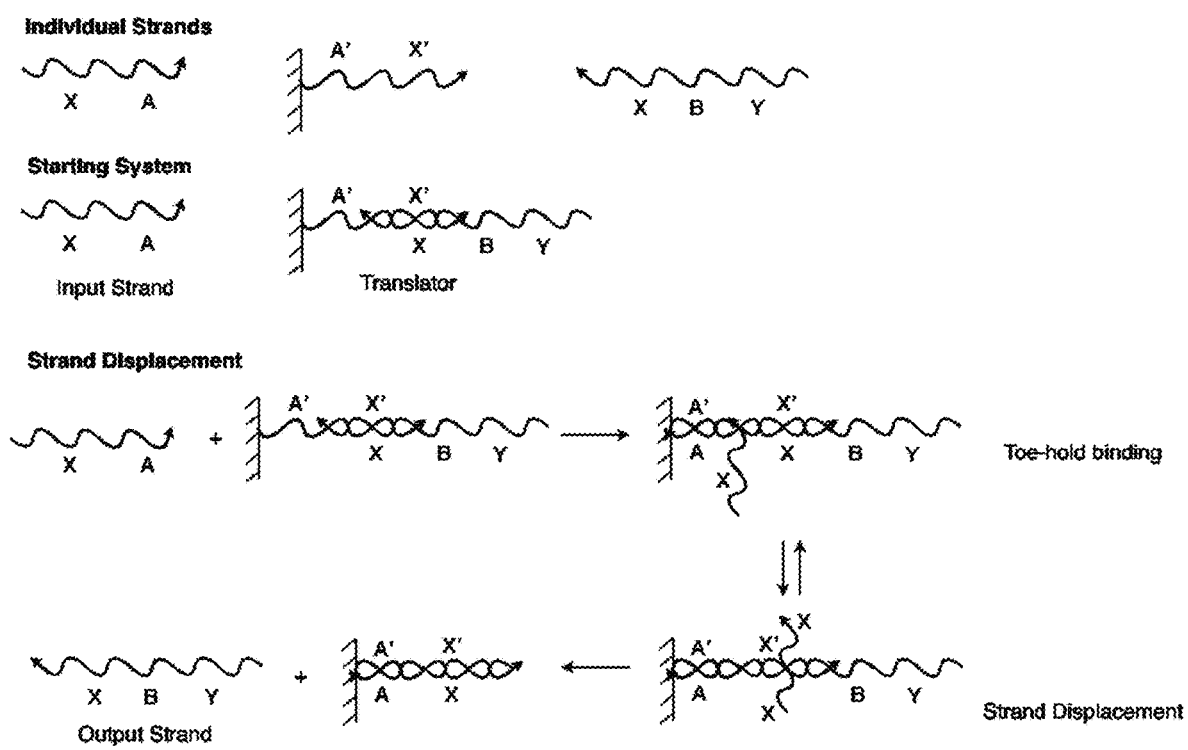
FIG. 1A illustrates a solid-phase sequestering implementation of a nucleic acid translator, where individual sections (A, B, etc) represent stretches of oligonucleotides of arbitrary length and sequence.

FIG. 1A shows a basic solid-phase sequestering setup for a translator, a component that allows a system to substitute one nucleic acid sequence for another. For the strand A'-X', each of A and X represents a stretch of oligonucleotides of arbitrary length and sequence, and X' and A' represent their respective reverse complements. Bound to a solid support, strand A'-X' is hybridized initially to Y-B-X, forming a nucleic acid structure in the form of an incompletely base-paired duplex, which can function as a translator. In this configuration the strand Y-B-X is solid-phase sequestered and, hence, cannot interact with the rest of the system. Yet, in the presence of the strand X-A, referred to as a "polynucleotide displacement molecule," strand Y-B-X can be displaced from the solid support and exposed to the solution phase of the system, while strand X-A is bound to the support. This operation involves two steps; the first is the hybridization of complementary sequences A and A' (often referred to as "toe-hold binding"). In the second step the X region of strand X-A binds to the X' region of A'-X', displacing the X region of Y-B-X and releasing this strand into solution while leaving X-A bound to the solid support (this step is often referred to as a "branch migration reaction"). This two-step process effectively allows for the translation of a free X-A strand into a free Y-B-X strand.

Figure 1B:
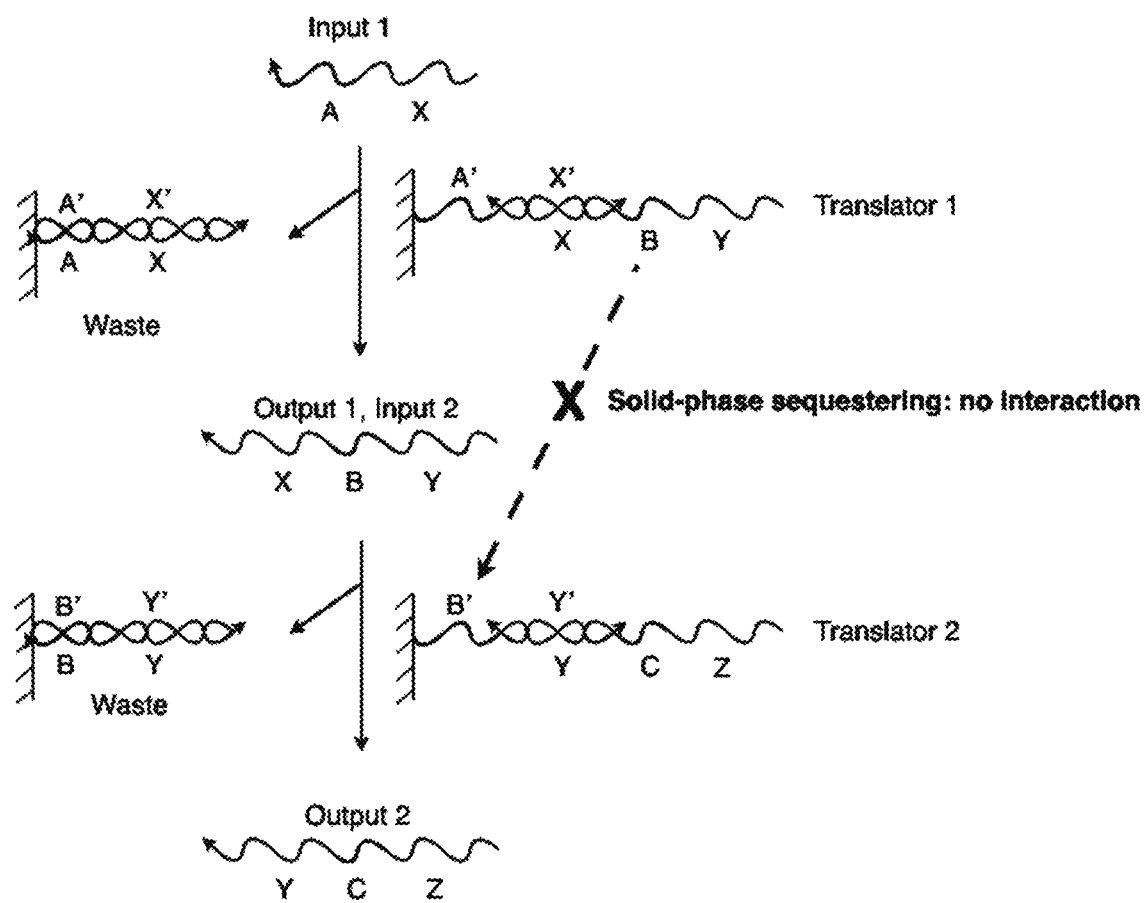
FIG. 1B illustrates how a solid-phase sequestering implementation of a nucleic acid translator sequesters stretches of oligonucleotides.

FIG. 1B shows a system having an input strand X-A interacting with an incompletely base-paired duplex, "Translator 1." The output includes a completely base-paired duplex, A'-X'/X-A, which is considered a "waste" product, and an output strand Y-B-X, which is referred to as "Output 1" and can be used as "Input 2" in a further reaction. "Input 2" interacts with "Translator 2" and produces the "Output 2" and another waste product. In this figure, the B region of strand Y-B-X illustrates the sequestering of sequences in this network. At the start, Y-B-X cannot hybridize with the B' region of Translator 2 because both are isolated on separate solid-supports. When Input 1 binds to Translator 1 and releases Y-B-X into solution, Y-B-X can then interact with Translator 2. Therefore, the ability of Y-B-X and Translator 2 to interact is conditional on the presence of Input 1.

The strands bound to one solid surface interact extremely slowly with strands on another solid surface due to steric effects. Consequently, the strands in the solution phase are the only components that can interact with the solid phase operators.

Toe-Hold Sequestering

Toe-hold sequestering accomplishes the same operations as solid-phase translators, but functions by keeping stretches of sequence bound up in a duplex. Just as in the solid-phase translator, a displacement event can free the sequence of interest. All of the strands can be in solution together, by the consequence of which displacement events are regulated by the availability of toe-holds. The term "toe-hold" here refers to short stretches of single-strand nucleic acid sequences that provide a starting point for a displacement event.

Figure 2A:
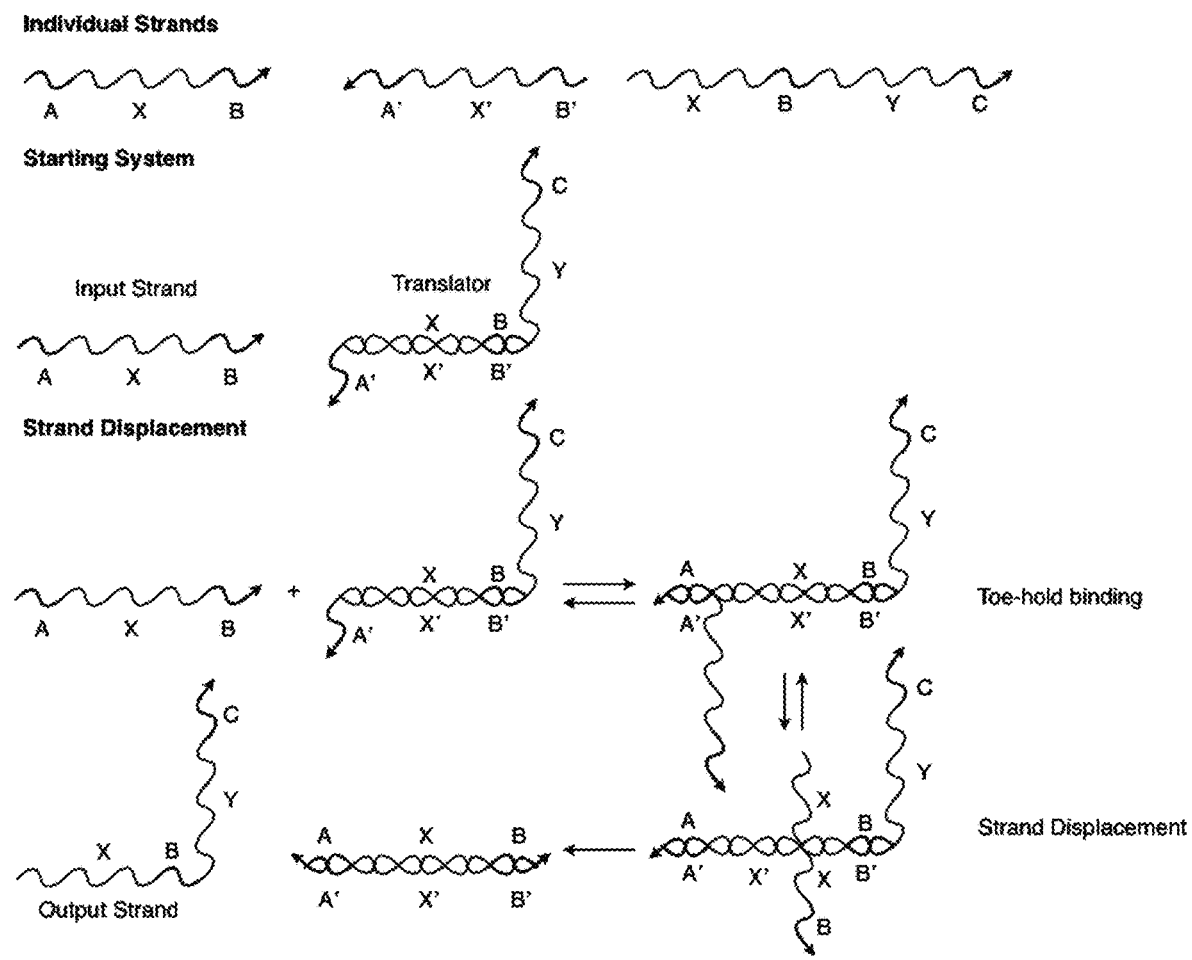
FIG. 2A illustrates a "toe-hold" sequestering implementation of a nucleic acid translator. Again, individual sections represent stretches of oligonucleotides of arbitrary length and sequence.

FIG. 2A shows a toe-hold sequestered translator similar to the one in FIG. 1A, but based on toe-hold rather than solid-phase sequestering. In this example, the A' region of the translator is the toe-hold that binds the input strand and allows the strand displacement reaction to proceed.

Figure 2B:
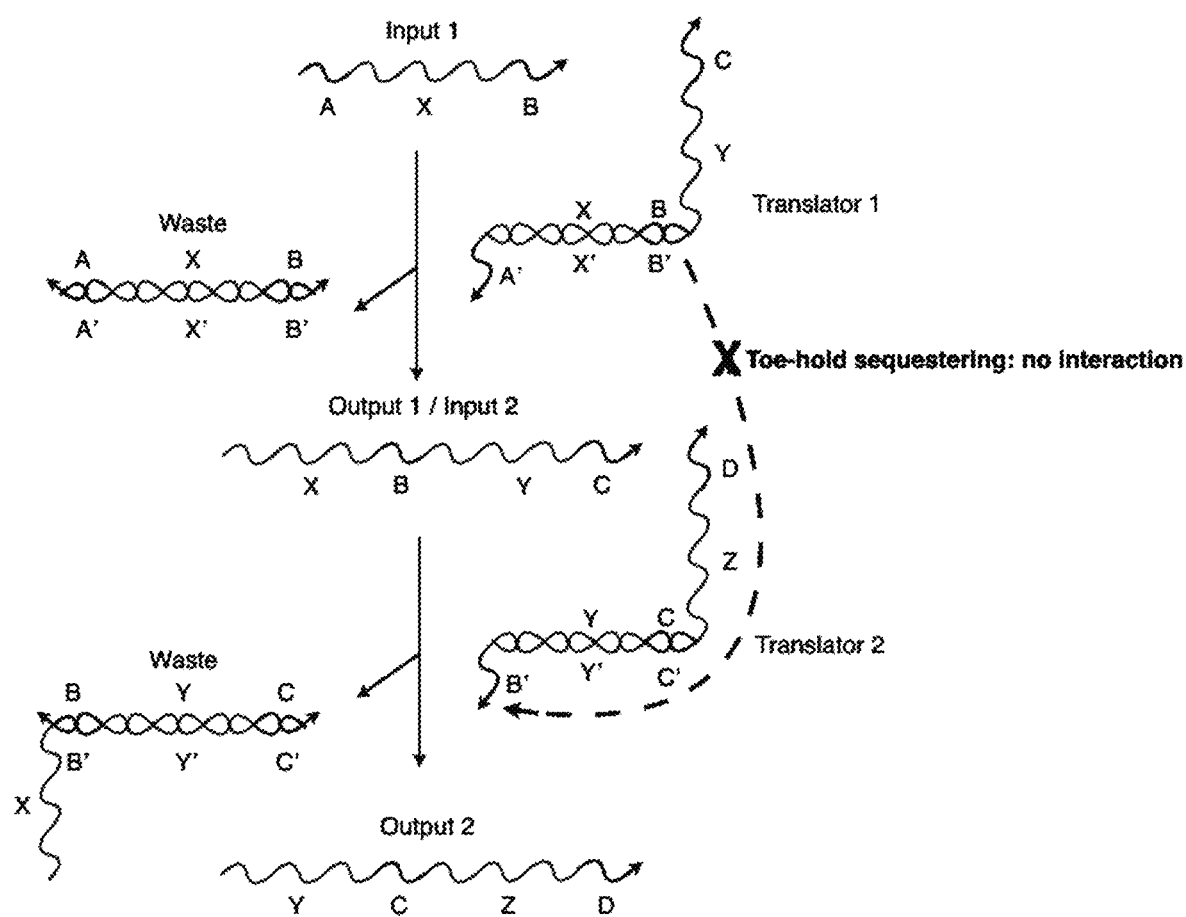
FIG. 2B illustrates how the toe-hold-sequestered implementation shown in FIG. 2A sequesters stretches of oligonucleotides.

FIG. 2B shows a toe-hold-based system having an input strand A-X-B interacting with an incompletely base-paired duplex, "Translator 1." The output includes a waste product, i.e., a completely base-paired duplex, B'-X'-A'/A-X-B, and "Output 1" strand X-B-Y-C, which can be used as "Input 2" in a further reaction. "Input 2" interacts with "Translator 2" and produces the "Output 2" and another waste product. In this figure, the B region of X-B-Y-C is sequestered in Translator 1 by being hybridized to a complementary B' region and therefore unable to interact with the B' region of Translator 2. The ability of X-B-Y-C to interact with Translator 2 is conditional on the presence of Input 1 (A-X-B) in the system.

While potentially very useful, applications of the toe-hold geometries have been limited to date by the rate at which a system containing such toe-hold geometries can propagate information. Inherent limitations in conventional toe-hold-sequestered approaches frequently can slow the resultant propagation down below a biologically useful timescale. More specifically, toe-hold sequestered translators work at reasonable speeds only in a narrow dynamic range of concentrations as a consequence of the clashing interactions. By tuning the length of toe-holds, clashing interactions can be made reversible at lower concentrations. As concentration increases, however, clashing would dominate, and the system would grind to a halt. If concentration decreases, on the other hand, toe-hold mediated displacement would also grind to a halt. In this context, it is noted that, in a biological context, concentrations can vary widely; hence such translators are poorly suited for use in the actual biological context. It is believed that kinetic bottlenecks are a result of unproductive reactions, referred to here as "toe-hold clashes," that occur when a toe-hold is bound by a molecule having a complementary sequence or "clashing strand" that cannot produce a displacement reaction.

Figure 3A:
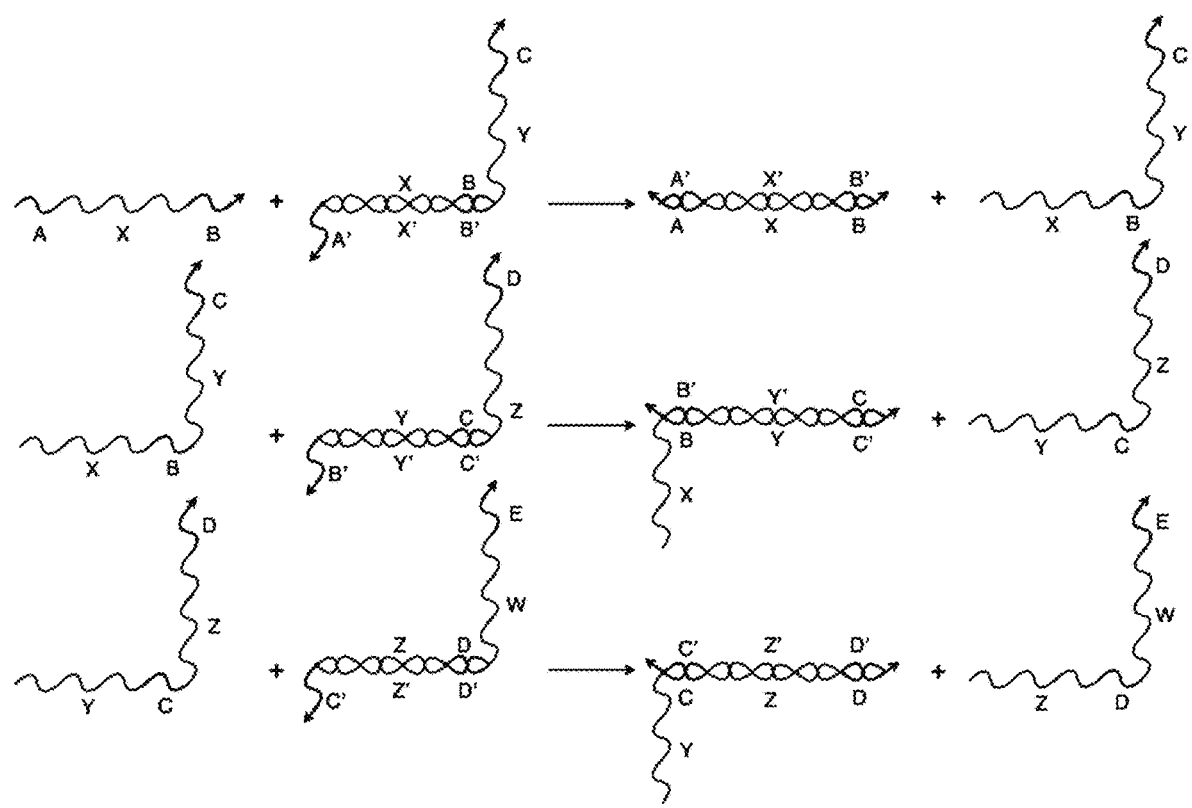
FIG. 3A shows a system of three toe-hold-sequestered nucleic acid translators. The reactions shown are all strand displacement reactions that proceed by the same branch-migration mechanism as in FIG. 2A.
Figure 3B:
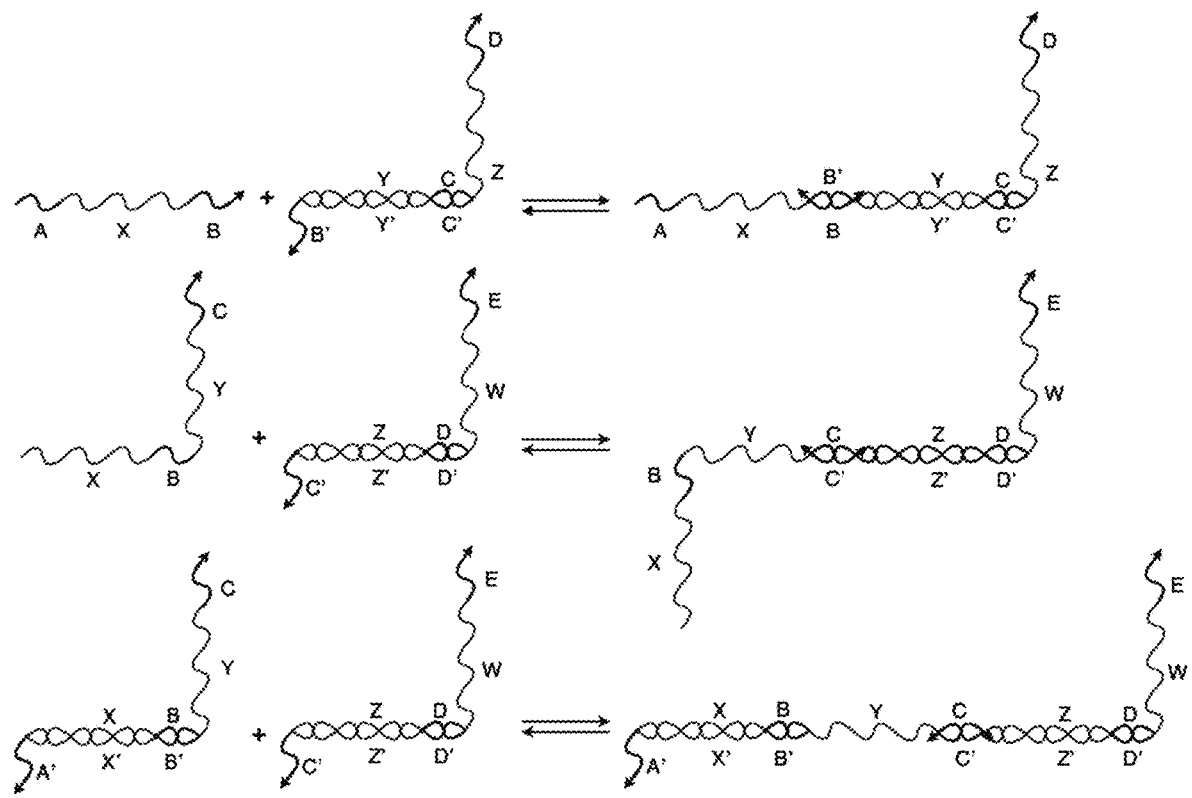
FIG. 3B shows a system with the same oligonucleotides shown in FIG. 3A but, instead of strand displacement reactions, toe-hold "clashes" are shown, where the toe-hold is bound by a sequence that cannot produce a strand displacement reaction. This binding event occupies the toe-hold such that the desired strand cannot bind.

For instance, FIG. 3A shows a system of three toe-hold sequestered nucleic acid translators, much like the one in FIG. 2A. If all three strands are in solution together, however, there are other binding events that can take place. FIG. 3B illustrates some of the non-productive binding events or clashes that can take place. By involving a "polynucleotide clashing molecule," these events do not lead to a displacement reaction but can slow the system down, because the incidence of a clashing strand blocks strands from binding that can produce a displacement reaction. Such clashing events can become more dominant when the concentrations of the nucleic acid translators increase in a system.

Another limitation of this approach is the potential toxicity resulting from exposure of the the large single-stranded regions of the translators. For instance, when a single-stranded region binds to endogenous DNA or RNA in a cell, it can alter transcription, translation, or other function of the DNA or RNA molecule. Such "off-target" event can lead to undesired consequences in the cell.

Figure 4:
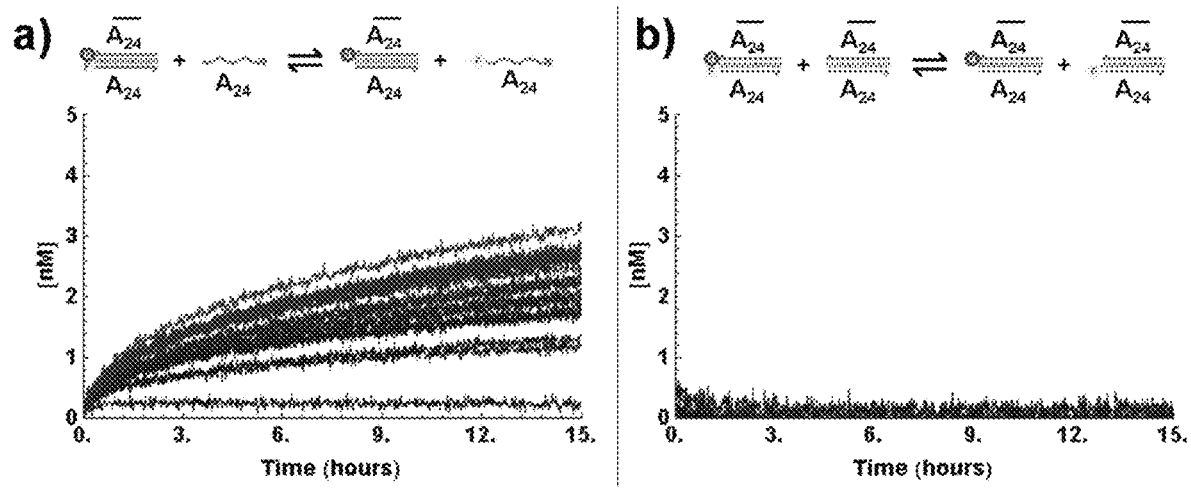
FIG. 4 shows exchange reactions with (a) or without (b) toe-holds in PBS buffer (137 mM NaCl, 2.7 mM KCl, 10 mM $Na_2HPO_4$, 1.76 mM $KH_2PO_4$, pH 7.4) at 37° C. Fluorescent signals were converted to concentrations through the use of a standard curve. a) 50 nM [F-$(A_{24})$::($\overline{A_{24}}$)-Q]$_0$ duplex was incubated with a titration of 10-200 nM [$(A_{24})$]$_0$ by increments of 10 nM (blue to red) and concentrations of free [F-$(A_{24})$]$_t$ were monitored via fluorescence resonance energy transfer (FRET). b) 50 nM [F-$(A_{24})$::($\overline{A_{24}}$)-Q]$_0$ duplex was mixed with a titration of 10-200 nM) [$(A_{24})$::($\overline{A_{24}}$)]$_0$ by increments of 10 nM (lower to higher) and concentrations of [F-$(A_{24})$::($\overline{A_{24}}$)]$_t$ were monitored via FRET.

Yet another limitation is the potential signal leak due to background reactions of translators in the absence of exposed toe-holds, which can also lead to undesired consequences. For instance, FIG. 4 at panel (a) shows that reactivity between a translator and a toe-hold goes up with the increase of concentration of the toe-hold. In the absence of the toe-hold, however, background reactivity was also observed (FIG. 4, panel (b)).

One proposed solution is to keep toe-holds short to mitigate the effect of clashes on the system: the shorter the toe-hold is, the faster the on/off rate of the complementary sequence can be. Thus, five or six nucleotide-long toe-holds are common because at these lengths, if a non-productive binding event occurs, the time spent in the double-stranded, "clashed" state is short.

This approach creates the aforementioned kinetic bottleneck, however, because the productive binding event is constrained by the same thermodynamic parameters; hence, the incoming strand likewise does not bind strongly to these toe-holds. Consequently, the desired displacement does not always occur when the correct incoming strand binds, as it needs to be in the bound state long enough to initiate the displacement reaction. The use of short toe-holds thus increases the amount of time required for a given operation to occur and produce an output. Put another way, the displacement reaction cannot take place before the occurrence of many binding events, both by clashing strands and by desired strands. This inefficiency limits the utility of the system by slowing down the propagation of information to time scales that are too extended to be useful.

Shorter toe-holds, along with shorter single-stranded regions on the translators, can also help reduce toxicities. However, the shorter toe-holds do not solve the problem with signal leak.

Toe-Hold Exchange

Figure 5:
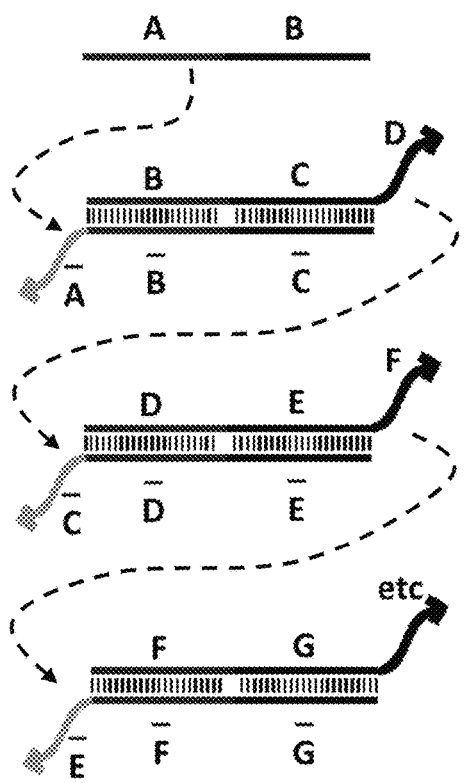
FIG. 5 illustrates a toe-hold exchange approach for designing translators.

"Toe-hold exchange," uses similar pairing interactions as toe-hold sequestering but with different geometrics. Toe-hold exchange attempted to solve the toe-hold clash problem posed by the toe-hold sequestering approach. With reference to FIG. 5, the initial toe-hold, A-B, is only partially complementary to a single-stranded region in the duplex right below the toe-hold (i.e., A::A). Likewise, when the B-C-D toe-hold is generated through an exchange reaction with the A-B toe-hold, the B-C-D toe-hold is only partially complementary to the single-stranded region of the duplex below it too. As such, no toe-hold clash would occur.

The toe-hold exchange approach has inherent limitations too, however. First, like in toe-hold sequestering, the long single-stranded regions of the translators can cause undesired toxic effect due to off-target binding to endogenous nucleic acids in a cell.

Another issue relates to the dynamic range of the translation which is similar to, albeit not the same as, the issues encountered in toe-hold clashing. This issue is less severe with toe-hold exchange, though, since it impacts speed of translation more so than yield. In this case the lengths of the toe-holds determine the rate of spontaneous dissociation, which is faster with shorter toe-holds. On the other hand, they also determine the forward displacement rate, but longer toe-holds make forward displacement faster. Therefore, there is a balance between these constraints in a concentration dependent way.

An important limitation with the toe-hold exchange approach is the low yield, as all reactions are bi-directional, leading to no favoring of final product unless, for instance, the entire translation is coupled to an irreversible reaction at the end.

Rotationally Sequestered Translators

The present disclosure provides a series of translators that solve the problems posed by the approaches detailed above. With these translators, toxic off-target effects and background reactivity are minimized, toe-hold clashes can be avoided, the overall yield is close to complete, and the translation speed still is improved significantly.

Figure 6A:
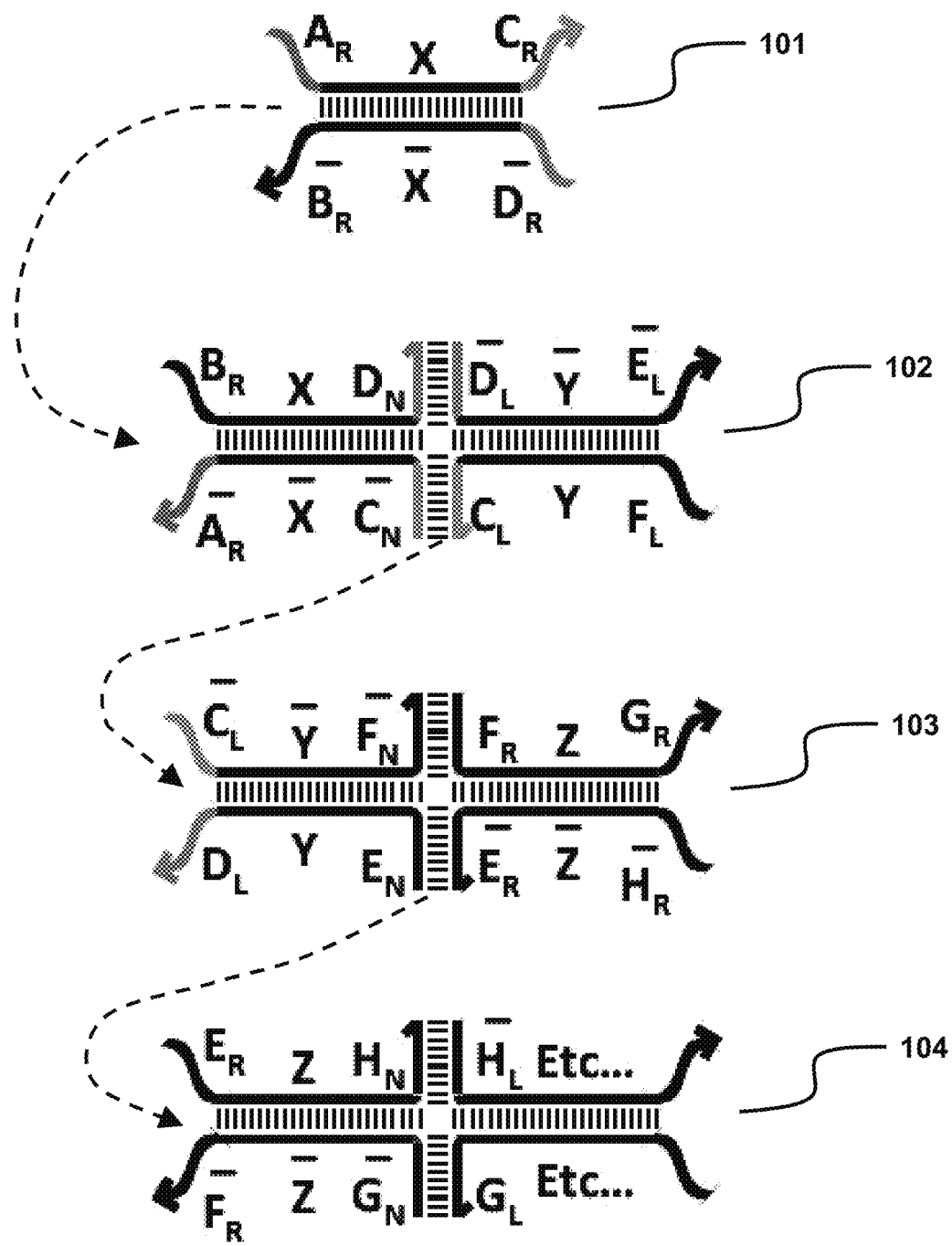
FIG. 6A-6B illustrate nucleic complexes (translators) employed by a rotational sequestering system.

FIG. 6A illustrates certain basic components in a "rotationally sequestered translator" system. On the top is a nucleic acid complex (101) formed between two strands, A-X-C and $\overline{D}$-$\overline{X}$-$\overline{B}$. By virtue of their sequence complementarity, a duplex region X::$\overline{X}$ is formed, whereas A, C, $\overline{D}$, and $\overline{B}$ remain single-stranded. Such a partial duplex then is referred to as a "dual toe-hold."

The second nucleic acid complex (102) shown in FIG. 6A is comprised of four nucleic strands, B-X-D, $\overline{C}$-$\overline{X}$-$\overline{A}$, $\overline{D}$-$\overline{Y}$-$\overline{E}$, and F-Y-C. As shown, these strands form four duplex regions between them, and leave four single-stranded regions at the ends. One of these four strands, $\overline{C}$-$\overline{X}$-$\overline{A}$, is complementary to one of the strands, A-X-C, in the first complex, whereas another strand, B-X-D, is complementary to $\overline{D}$-$\overline{X}$-$\overline{B}$, the other strand of the first complex, By virtue of sequence complementarity in the hanging single-stranded regions, the first complex (101) has suitable sequence complementarity so as to be capable of binding to the second complex (102), which initiates a strand displacement reaction that involves six strands. The output of the strand displacement reaction includes two completely annealed duplexes (105 and 106) and a new dual toe-hold (107), having a duplex region in the middle and four separate single-stranded regions (FIG. 6B).

Figure 6B:
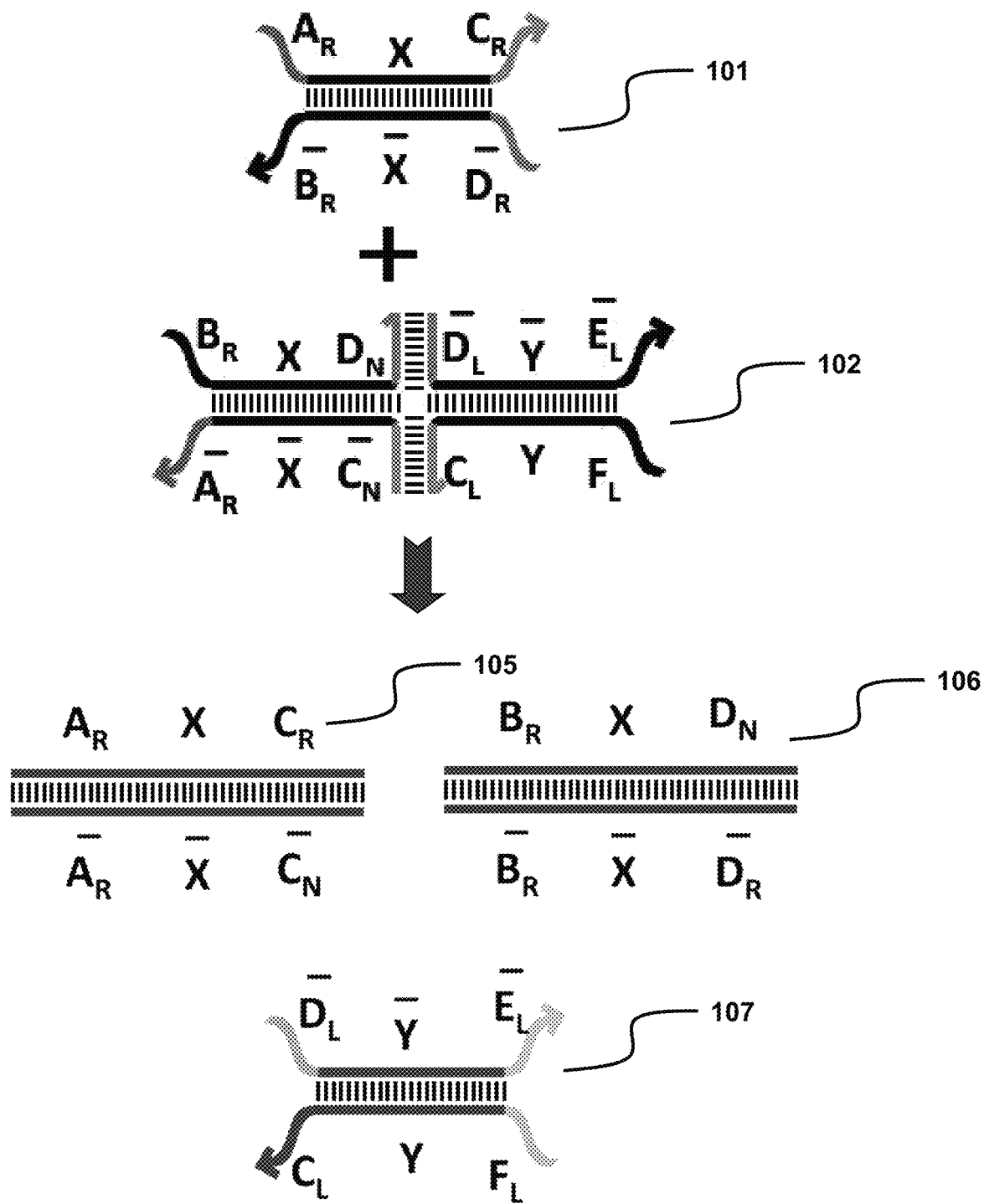

FIG. 6B shows that the output nucleic complexes (105, 106 and 107) are at a lower energy state, due to the two complete duplexes, A-X-C::$\overline{C}$-$\overline{X}$-$\overline{A}$ (105) and B-X-D::$\overline{D}$-$\overline{X}$-$\overline{B}$ (106). In other words, such a strand displacement strongly favors the forward direction and, hence, is not easily reversible.

The newly formed dual toe-hold, comprised of $\overline{D}$-$\overline{Y}$-$\overline{E}$ and F-Y-C (107), then can initiate another strand displacement reaction with the third nucleic complex (103) in FIG. 6A (see arrows), carrying on the translation process. Likewise, a new dual toe-hold generated from this displacement reaction can target the fourth complex (104), and so on.

As explained above, the strand displacement reactions in this approach achieve high yield rate because each of the reaction generates output products at a much lower energy state than the input nucleic acid molecules. As Table 1 illustrates, moreover, experimental data show that such dual toe-hold-mediated reactions can be quite fast as well. Compare the column of "Dual Toe-Holds" to the ones identified as "3' Toe-hold" or "5' Toe-hold".

TABLE 1

Comparison of reaction speed between single toe-hold-
and dual toe-hold-medicated strand displacement reactions

| Toe-hold Length (nt) | Observed Half-Life of [50 nM]$_0$ Reaction | | | | |
|---|---|---|---|---|---|
| | Strand Exchange | | Duplex Exchange | | |
| | 3' Toe-hold | 5' Toe-hold | 3' Toe-hold | 5' Toe-hold | Dual Toe-Holds |
| 25 | ~30 minutes | ~30 minutes | ~2 hours | ~1 hour | ~15 minutes |
| 20 | ~45 minutes | ~30 minutes | ~2 hours | ~1 hour | ~15 minutes |
| 15 | ~30 minutes | ~30 minutes | ~2 hours | ~1 hour | ~15 minutes |
| 10 | ~15 minutes | ~15 minutes | >15 hours | >15 hours | ~15 minutes |
| 9 | ~15 minutes | ~15 minutes | >15 hours | >15 hours | ~15 minutes |
| 8 | ~15 minutes | ~15 minutes | >15 hours | >15 hours | ~15 minutes |
| 7 | ~15 minutes | ~15 minutes | >15 hours | >15 hours | ~30 minutes |
| 6 | ~15 minutes | ~3 hours | >15 hours | >15 hours | ~5 hours |
| 5 | ~45 minutes | >15 hours | >15 hours | >15 hours | ~2 hours |
| 4 | ~3 hours | ~9 hours | >15 hours | >15 hours | >15 hours |
| 3 | >15 hours | >15 hours | >15 hours | >15 hours | >15 hours |
| 2 | >15 hours | >15 hours | >15 hours | >15 hours | >15 hours |
| 1 | >15 hours | >15 hours | >15 hours | >15 hours | >15 hours |
| 0 | >15 hours | >15 hours | >15 hours | >15 hours | >15 hours |

In accordance with these findings, the present disclosure provides a number of translators and translator sets, sometimes referred to as "adaptors." A translator or translator set takes a nucleic acid molecule (e.g., single stranded nucleic acid, complete or partially duplex nucleic acids, or more complex nucleic acid structure or translators) as input and carries out one or more strand displacement reactions to produce one or more nucleic acid molecules as outputs. Each of these inputs or outputs can serve as outputs or inputs to other translators or translator sets in a system. Each of these translators and translator sets therefore functions as a logic operator and, in combination, carries out desired computation and information conveyance.

For instance, in FIG. 6B translator 102 takes a partial duplex, toe-hold 101 as an input and undergoes a series of strand displacement reactions, leading to the release of three different nucleic acid molecules, duplexes 105 and 106 and a new toe-hold 107. Here the new toe-hold 107 (i.e., the distal/right-hand-side half of translator 102) can serve as an input to other translators. The production of the complex duplexes 105 and 106, due to their high stability, helps drive the displacement reactions to completion to the desired direction.

Accordingly, in one embodiment the present disclosure provides a composition comprising first and second nucleic acid complexes, each comprising first, second, third, and fourth nucleic acid strands. Each of the strands comprises sequentially (i.e., from 5' to 3', consecutively or separated with intermediate nucleotides) a first fragment, a second fragment and a third fragments, where the nucleic strands are defined as:

B-X-D, $\overline{C}$-$\overline{X}$-$\overline{A}$, $\overline{D}$-$\overline{Y}$-E and F-Y-C for the first, second, third and fourth strands of the first complex, respectively, and $\overline{C}$-$\overline{Y}$-$\overline{F}$, E-Y-D, F-Z-G, $\overline{H}$-$\overline{Z}$-$\overline{E}$ for the first, second, third and fourth strands of the second complex, respectively.

Each letter denotes a fragment and each string of letters connected by "-" denotes a strand.

In one aspect, each of the first and the second complexes comprises a first duplex region formed between the second fragments of the first and second strands (X::$\overline{X}$ and $\overline{Y}$::Y, in the first and second complexes, respectively), a second duplex region formed between the second fragments of the third and fourth strands (Y::$\overline{Y}$ and Z::$\overline{Z}$), a third duplex region formed between the third fragment of the first strand and the first fragment of the third strand (D::$\overline{D}$ and $\overline{F}$::F), and a fourth duplex region formed between the first fragment of the second strand and the third fragment of the fourth strand ($\overline{C}$::C and E::$\overline{E}$).

In each of the first and second complexes, the first fragment (B and $\overline{C}$, in the first and second complexes, respectively) of the first strand, the third fragment ($\overline{A}$ and D) of the second strand, the third fragment (E and G) of the third strand and the first fragment (F and $\overline{H}$) of the fourth strand are single-stranded.

Further, the third strand of the first complex ($\overline{D}$-$\overline{Y}$-E) has suitable sequence complementarity to the second strand of the second complex (E-Y-D) to allow binding therebetween under hybridizing conditions; and the fourth strand of the first complex (F-Y-C) has suitable sequence complementarity to the first strand of the second complex ($\overline{C}$-$\overline{Y}$-$\overline{F}$) to allow binding therebetween under hybridizing conditions.

In one aspect, the composition further comprises a third nucleic acid complex comprising a first and a second nucleic acid strands, each of the strands comprising, sequentially, a first, a second and a third fragments, wherein the first and second strands are defined as E-Z-H and $\overline{G}$-$\overline{Z}$-$\overline{F}$ respectively, wherein the third nucleic acid complex comprises a duplex region formed between the second fragments of the first and second strands (Z::$\overline{Z}$) and the first fragment (E) of the first strand and the third fragment of the second strand ($\overline{F}$) are singled-stranded, and wherein: the third strand of the second complex (F-Z-G) has suitable sequence complementarity to the second strand of the third complex ($\overline{G}$-$\overline{Z}$-$\overline{F}$) to allow binding therebetween under hybridizing conditions; and the fourth strand of the second complex ($\overline{H}$-$\overline{Z}$-$\overline{E}$) has suitable sequence complementarity to the first strand of the third complex (E-Z-H) to allow binding therebetween under hybridizing conditions.

Chemical Modifications to Avoid Toe-Hold Clashing

The present disclosure also provides a methodology for preventing toe-hold clashing. As shown in FIG. 6A, toe-hold clashing still can occur between, e.g., the toe-hold (101) and complex (103) due to the exposed single-stranded regions, C/$\overline{D}$ and $\overline{C}$/D.

In one such method, each nucleic acid fragment that can potentially be exposed as single-stranded during the translation process is subject to potentially chemical modification. In addition to its natural state (state N, annotated as subscript in, e.g., $C_N$), each of such fragment can be modified to form two states, states R (e.g., right-handed) and L (left-handed), respectively, so long as such modifications allow (or promote) and prohibit (or inhibit) binding between complement strands of certain states as shown in Table 2 below.

TABLE 2

Binding objectives for the chemical modifications

| Modification of one strand | Modification of the complement strand | Allow/inhibit binding |
|---|---|---|
| N | N | Allow |
| N | R | Allow |
| N | L | Allow |
| R | R | Allow |

TABLE 2-continued

Binding objectives for the chemical modifications

| Modification of one strand | Modification of the complement strand | Allow/inhibit binding |
|---|---|---|
| R | L | Inhibit |
| L | L | Allow |

With such modifications, in one aspect the tail fragment ($\overline{E}_L$) of the third strand of the first complex (102) has reverse sequence complementarity with the head fragment (ER) of the first fragment of the first strand of the third complex (104), but does not stably bind to it. Likewise, in another aspect the head fragment (FL) of the fourth strand of the first complex (102) has reverse sequence complementarity with the tail fragment ($\overline{F}_R$) of the first fragment of the first strand of the third complex (104), but does not stably bind to it. Accordingly, no toe-hold clashing would occur and such modifications ensure that the displacement reactions occur in a controlled manner. In one aspect, therefore, the term "rotational" is used to refer to the modifications (L and R) that modulate the sequestering, rather than the exchange reactions employed.

As used herein, the term "does not stably bind" indicates that two nucleic acid strands do not form a stable duplex structure, even if they share sequence complementarity. A "stable" duplex structure, in some aspects, refers to a duplex that can exist in a non-transient fashion at a concentration that is higher than 0.1%, or 1%, or 5%, or 10% of the total concentration of each individual strand in a reaction solution.

As further described below, chemical modifications are known that can achieve the binding objectives defined in Table 2. "Chemical modification" in this context is not limited to chemically modifying a nucleic acid molecule after it is produced; rather, the phrase also encompasses incorporating chemically modified nucleotides while producing the nucleic acid molecule.

There are many well-characterized nucleic acid modifications that can be used to modulate the thermodynamic properties of binding to natural DNA or RNA. These include changes to the backbone, sugar, or nucleobase of the oligonucleotide. The modifications also can be employed separately or in conjunction with one another; that is, using a modified backbone does not preclude the use of a modified nucleobase in the same strand.

Nucleic acid backbone analogs can be used to improve the binding of strands capable of producing a displacement reaction. There are a number of different analogs that could be used, all of which offer tighter binding affinities to DNA and RNA than natural nucleic acids. These analogs include but are not limited to those with uncharged backbones (peptide nucleic acids or phosphorodiamidates), positively charged backbones (guanidinium peptide nucleic acids), and hydrogen-bonding groups that allow for pre-organization (gamma peptide nucleic acids). In one aspect, the backbones include mini-PEG-conjugated, serine-derived gamma-PNAs, as illustrated in FIG. 7f-g.

Figure 7:
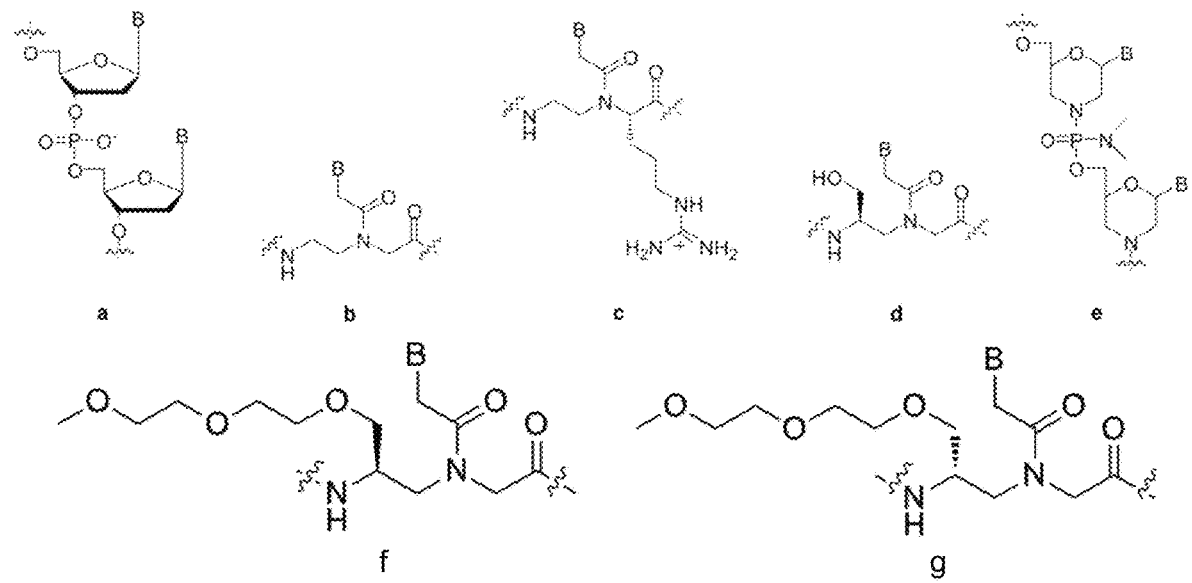
FIG. 7 shows modified backbone structures for nucleic acid analogs, where "B" represents an arbitrary nucelobase, and (a) shows a natural phosphodiester backbone found in DNA, (b) shows peptide nucleic acids, (c) shows guanidinium peptide nucleic acids, (d) shows L-serine derived gamma-PNAs, (e) shows phosphorodiamidates (here with a morpholino sugar), and (f) and (g) show mini-PEG-conjugated, serine-derived gamma-PNAs.

General structures for certain analogs are shown in FIG. 7. These analogs all improve the thermodynamics of nucleic acid hybridization reactions, allowing for tighter toe-hold binding and therefore faster displacement. By using these analogs in specific places of the logic network, the desired displacement reactions can be strongly favored in comparison to the clashing interactions, thus accelerating the rate of desirable strand displacement reactions.

Figure 8:
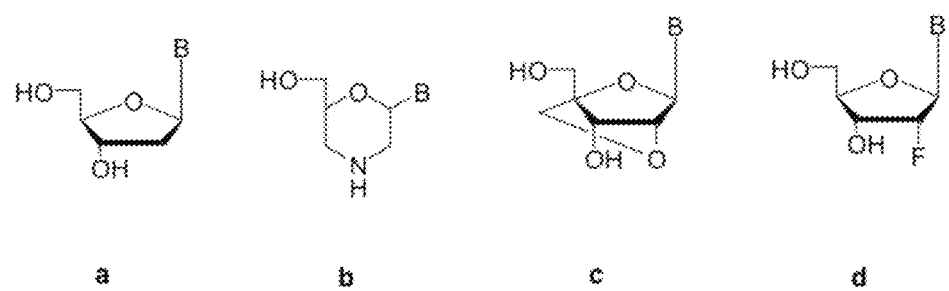
FIG. 8 illustrates modified sugar structures for nucleic acid analogs, where "B" represents an arbitrary nucleobase, and (a) shows a natural deoxyribose sugar found in DNA, (b) shows morpholinos, (c) shows locked nucleic acids, and (d) shows fluorine-modified RNA derivative.

The use of modified sugar rings can also alter the thermodynamics of binding to DNA or RNA for an oligonucleotide. The most widely used analogs are morpholinos, locked nucleic acids (LNAs), and LNA derivatives. Other modified sugars are documented in the literature that also could produce a similar result, in terms of altering binding thermodynamics. Illustrative of these are sugars with modifications at the 1', 2', 3' or 4' position and sugars with different atoms substituted for the oxygen in the ribose cyclopentane ring. These analogs are illustrated in FIG. 8.

Figure 9:
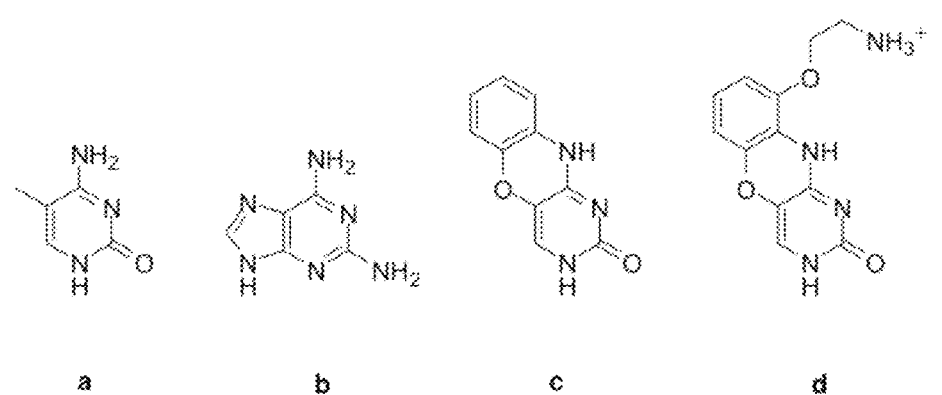
FIG. 9 illustrates modified nucelobase structures for the nucleic acid analogs methylcytosine (a), diaminopurine (b), phenoxazine (c), and G-clamp (d)

Nucleobase modifications can also be used to achieve the same effect as backbone and sugar analogs; namely, altering the thermodynamics of specific hybridization reactions. These bases include methylcytosine, diaminopurine, G-clamp, and phenoxazine (FIG. 9), all of which improve the binding affinity of a strand for its reverse complement. Another opportunity that exists with nucleobase modification involves pseudocomplementary bases. This class of base analogs forms weak base pairs with one another but forms strong base pairs with standard bases. One such pair of bases is 2-aminoadenine (nA) and 2-thiothymine (sT). These bases could be used to favor one strand binding while disfavoring another, an example of increasing the likelihood of a productive binding event while decreasing the likelihood of a clash at the same time.

Another chemical modification that could be used to alter the thermodynamics of binding interactions is the incorporation of charged polymers like chitosan, which has been shown in the literature to accelerate the rate of displacement reactions. However, since these polymers speed up reactions non-specifically, they would have to be used in conjugation with one of the other modifications mentioned above to allow for discrimination between desired and undesired binding events.

Different approaches can be used to synthesize the molecules with the chemical modifications discussed above. For example, the backbone chemistry can be taken into consideration of the design of the modified molecules. Backbone chemistry is what is used to put together individual monomers into a longer strand. Modifications that involve the nucleobase or the sugar but that keep the natural phosphodiester backbone of DNA/RNA can be synthesized via standard phosphoramidite chemistry, as employed for natural monomers. Illustrations of these methods are found, for example, in Beaucage, S., and R. Iyer, *Tetrahedron* 48: 2223 (1992), in Brown, D. M. A, "Brief history of oligonucleotide synthesis," 20 METHODS IN MOLECULAR BIOLOGY (Protocols for Oligonucleotides and Analogs) 1-17 (1993), in Reese, Colin B., *Organic & Biomolecular Chemistry* 3: 3851 (2005), and in Iyer, R. P.; and S. L. Beaucage, "7.05. Oligonucleotide synthesis," 7 COMPREHENSIVE NATURAL PRODUCTS CHEMISTRY (DNA and Aspects of Molecular Biology) 105-52 (1999). The respective contents of the foregoing publications are hereby incorporated by reference in their entirety here.

If the backbone is changed in a particular modification, a different chemistry will be employed. Such modification chemistry is described in the scientific literature. Thus, peptide nucleic acids (PNAs) and their derivatives rely on amide bonds to link the individual monomers together. Instead of using phosphoramidite chemistry, therefore, strands of these monomers are made with amide bonding forming conditions and coupling reagents like HBTU. An exploration of the methods used to make PNA or PNA-like oligonucleotides can be found, for instance, in F. Beck, "Solid Phase Synthesis of PNA Oligomers," METHODS IN MOLECULAR BIOLOGY SERIES (Peptide Nucleic Acids), Humana Press, http://www.springerlink.com/content/mr571738x7t65067/.

These chemical modifications include introduction of handedness into a DNA or PNA fragment. Handedness of DNA, particularly of PNA, is a well-characterized feature, and methodology for generating handedness also is known. See, e.g., Corradini et al. "Control of helical handedness in DNA and PNA nanostructures," METHODS MOL BIOL. 749:79-92 (2011). Left-handed DNA or PNA is precluded from binding to right-handed DNA or PNA, whereas both can bind to their natural counterparts.

Another backbone modification approach involves chimeric oligonucleotides. These are oligonucleotide strands that contain different backbone chemistries in the same molecule. For example, if one needed a strand that was half PNA backbone and half DNA backbone, one would need a way to join these two different backbone chemistries. Making these chimeric strands is also generally known in the art. In the above example of a PNA/DNA chimera, the difference in chemistries can be bridged by using modified DNA or PNA monomers. For DNA, the 5'-dimethoxytrityl (DMT) protected hydroxyl is replaced with a monomethoxytrityl (MMT)-protected amine that can react with the carboxylic acid of a PNA after deprotection. For PNA, the protected N-terminal nitrogen is replaced with a DMT-protected hydroxyl that can react with the phosphoramidite group on DNA after de-protection. These approaches are further described, for instgance, in E. Uhlmann et al., *Angew. Chem.* (Int'l ed.) 37: 2796-823 (1998).

All of these modifications, whether used individually or in conjunction with one another, can affect the thermodynamic conditions of specific interactions in an arbitrary nucleic acid network such that the binding of desired strands or complexes is favored over clashing interactions without altering sequence content. All of these interactions can apply to any branch-mediated migration reaction, whether they are 3-way branch migrations, such as solid-phase sequestering, toe-hold sequestering, or toe-hold exchange, or are branch migrations that take place by other mechanisms, e.g., four-way branch migration, four-way accelerated branch migration, or multi-strand complex migration.

Adaptors and Translator Sets

Translators provided in this disclosure can be used to build nucleic acid computers, which can be useful medically. For instance, the translators can "sense" the presence of a viral nucleic acid and then carry out a series of translation events, resulting in the "release" of a regulatory RNA (e.g., siRNA, antisense RNA) that can be used to initiate an antiviral response or apoptosis of the host cell, in order to eliminate the virus.

I. mRNA Adaptor

"Sensing" can be implemented as initiation of one or more strand displacement reactions, taking a nucleic acid (e.g., viral DNA/RNA, tumor DNA/RNA) as input, and releasing one or more toe-holds as output. The translators that carry out such one or more strand displacement reactions are termed "adaptors." In the case of a sensing a tumor mRNA, for instance, such an adaptor can be called a "mRNA adaptor."

Figure 10:
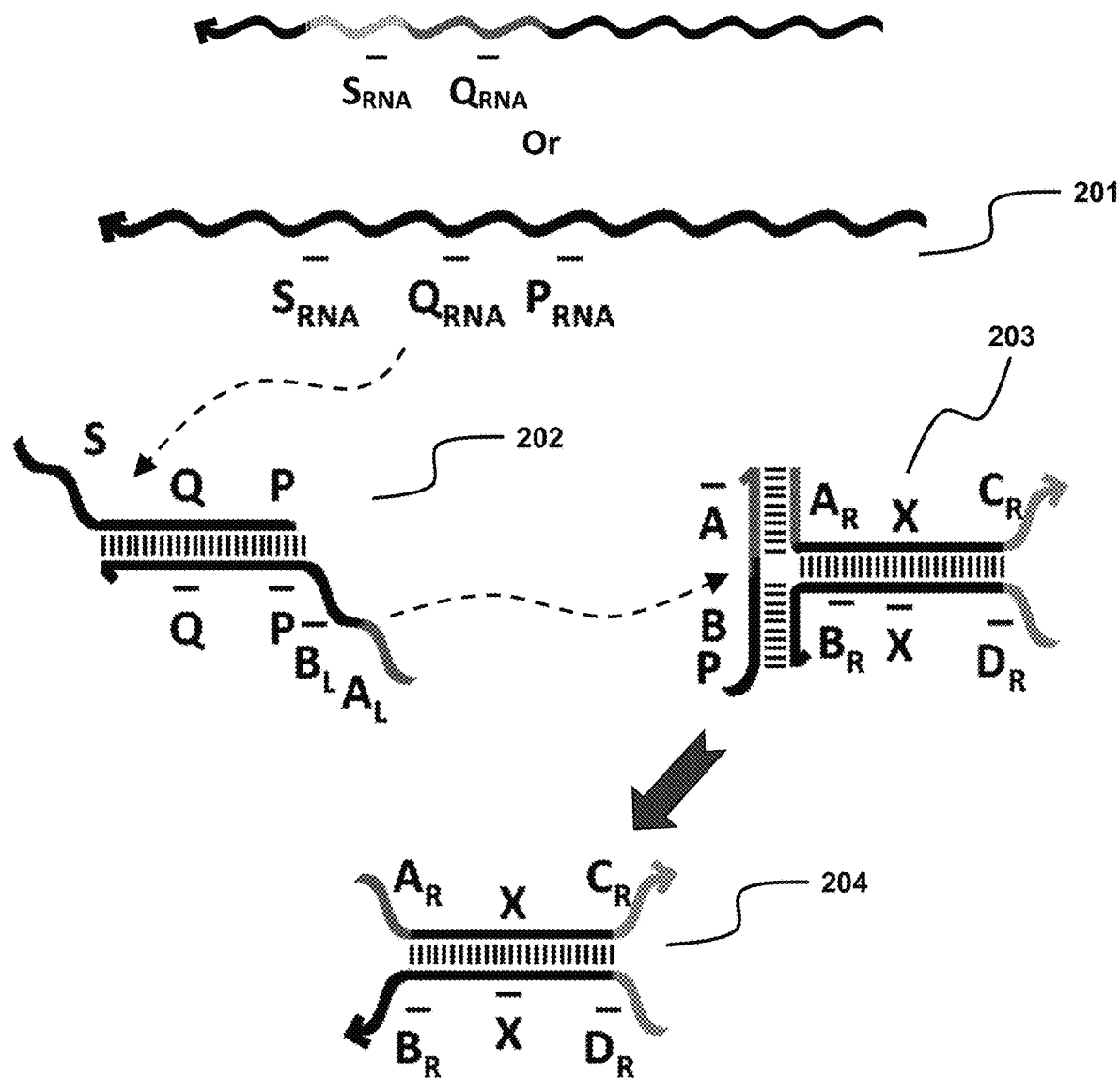
FIG. 10 depicts an mRNA adaptor.

An mRNA adaptor is illustrated in FIG. 10. A unique sequence on the mRNA (201) is identified having a stretch of fragments, $\overline{R}_{RNA}$-$\overline{P}_{RNA}$, or $\overline{R}_{RNA}$-$\overline{P}_{RNA}$-$\overline{Q}_{RNA}$. A first nucleic complex (202) of the mRNA adaptor is designed to include two strands, one of which has a complementary sequence (S-Q-P) to the mRNA. The other stand, also as shown in FIG. 10, forms a duplex region with the first strand (Q-P::$\overline{P}$-$\overline{Q}$), and has a single-stranded region, A-$\overline{B}$.

The second complex in the mRNA adaptor (203) includes at least three strands. A first strand (P-B-$\overline{A}$) is partially complementary to the second strand of complex 202, forming two separate duplex regions ($\overline{A}$::A and B::$\overline{B}$) with the second and third strands. In the absence of the first strand, the second and third strands take the form of a dual toe-hold as described above.

In a cell that contains the mRNA adaptor that includes complexes 202 and 203, therefore, upon presence of mRNA molecule 201 the mRNA initiates a strand displacement reaction with complex 202, thus releasing the second strand (A-$\overline{B}$-$\overline{P}$-$\overline{Q}$). The released strand then targets complex 203, resulting in a strand displacement reaction releasing a complex (204) that includes the second and third strands, in the form of a dual toe-hold. Such a dual toe-hold (204) is then capable of initiating additional strand displacement reactions as described herein. See, e.g., FIG. 6A.

Such an "mRNA adaptor" does not just sense an mRNA molecule. It can sense any single-stranded nucleic acid, including without limitation viral DNA and mutated tumor DNA.

Accordingly, the present disclosure provides a composition comprising a first nucleic acid complex (e.g., 202 in FIG. 10) and a second nucleic acid complex (203). The first complex (202) comprises (a) a first strand comprised of, sequentially, a first fragment (S), a second fragment (Q), a third fragment (P), and a fourth fragment (Q), and (b) a second strand comprised sequentially of a first fragment (A), a second fragment ($\overline{B}$), a third fragment ($\overline{P}$), and a fourth fragment ($\overline{Q}$). The first complex comprises a duplex region formed between the second and third fragments (Q-P) of the first strand and the third and fourth fragments ($\overline{P}$-$\overline{Q}$) of the second strand.

Further, the second complex (203) comprises (a) a first strand comprised of, sequentially, a first fragment (P), a second fragment (B) and a third fragment ($\overline{A}$) that have suitable sequence complementarity to the first (A), second ($\overline{B}$) and third ($\overline{P}$) fragments of the second strand of the first complex, respectively, to allow binding therebetween under hybridizing conditions, (b) a second strand comprised of, sequentially, a first fragment (A), a second fragment (X), and a third fragment (C) and (c) a third strand comprised sequentially of a first fragment ($\overline{D}$), a second fragment ($\overline{X}$), and a third fragment ($\overline{B}$). The second complex (203) comprises a first duplex region formed between the third fragment ($\overline{A}$) of the first strand and the first fragment (A) of the second strand, a second duplex region formed between the second fragment (B) of the first strand and the third fragment ($\overline{B}$) of the third strand, and a third duplex region formed between the second fragment (X) of the second strand and the second fragment ($\overline{X}$) of the third strand.

Chemical modifications to nucleic acid fragments that can be exposed as single strands are contemplated, as illustrated in FIG. 10, to reduce or avoid toe-hold clashing.

In accordance with one aspect of the disclosure, one embodiment of the disclosure provides a composition comprising: (a) a first nucleic acid complex comprising (i) a first nucleic strand comprising, sequentially, a first, second and third fragments and defined as S-Q-P, wherein each letter denotes a fragment and a string of letters connected by "-" denotes a strand, and (ii) a second strand comprising, sequentially, a first, second, third and fourth fragments and defined as A-$\overline{B}$-$\overline{P}$-$\overline{Q}$, wherein the first complex comprises a duplex region (Q-P::$\overline{P}$-$\overline{Q}$) formed between the second and third fragments of the first strand and the third and fourth fragments of the second strand; and (b) a second nucleic acid complex comprising (i) a first nucleic acid strand comprising, sequentially, a first, second and third fragments and defined as P-B-$\overline{\text{A}}$, (ii) a second nucleic acid strand comprising, sequentially, a first, second and third fragments and defined as A-X-C, and (iii) a third strand comprising, sequentially, a first, second and third fragments and defined as $\overline{\text{D}}$-X-$\overline{\text{B}}$, wherein the second complex comprises a first duplex region ($\overline{\text{A}}$::A) formed between the third fragment of the first strand and the first fragment of the second strand, a second duplex region (B::$\overline{\text{B}}$) formed between the first fragment of the first strand and the third fragment of the third strand, and a third duplex region (X::$\overline{\text{X}}$) formed between the second fragment of the second strand and the second fragment of the third strand, wherein the first (S) fragment of the first strand of the first complex, the first (A) and second ($\overline{\text{B}}$) of the second strand of the first complex, the first fragment (P) of the third strand of the second complex, the third fragment (C) of the second strand of the second complex, and the first fragment ($\overline{\text{D}}$) of the third strand of the second complex are single-stranded; and wherein the first, second and third fragments (A, $\overline{\text{B}}$, $\overline{\text{P}}$) of the second strand of the first complex have suitable sequence complementarity to the third, second and first fragments ($\hat{\text{A}}$, B, P) of the first strand of the second complex to allow binding therebetween, under hybridizing conditions, respectively.

In one aspect, the first strand (S-Q-P-R) of the first complex has suitable sequence complementarity to a fragment on a nucleic acid of a pathogenic nucleic acid to allow binding therebetween under hybridizing conditions.

In one aspect, the pathogenic nucleic acid is a viral DNA, a viral RNA, a bacterial DNA, a bacterial RNA, a mutant tumor DNA, or a tumor RNA.

II. RNAi Adaptor

Further provided is an adaptor that takes a nucleic acid as input and an RNAi (e.g., siRNA) molecule as output, so that the siRNA, upon release, can carry out the intended biological functions. Such an adaptor is illustrated in FIG. 11, and includes complexes 303 and 304.

Figure 11:
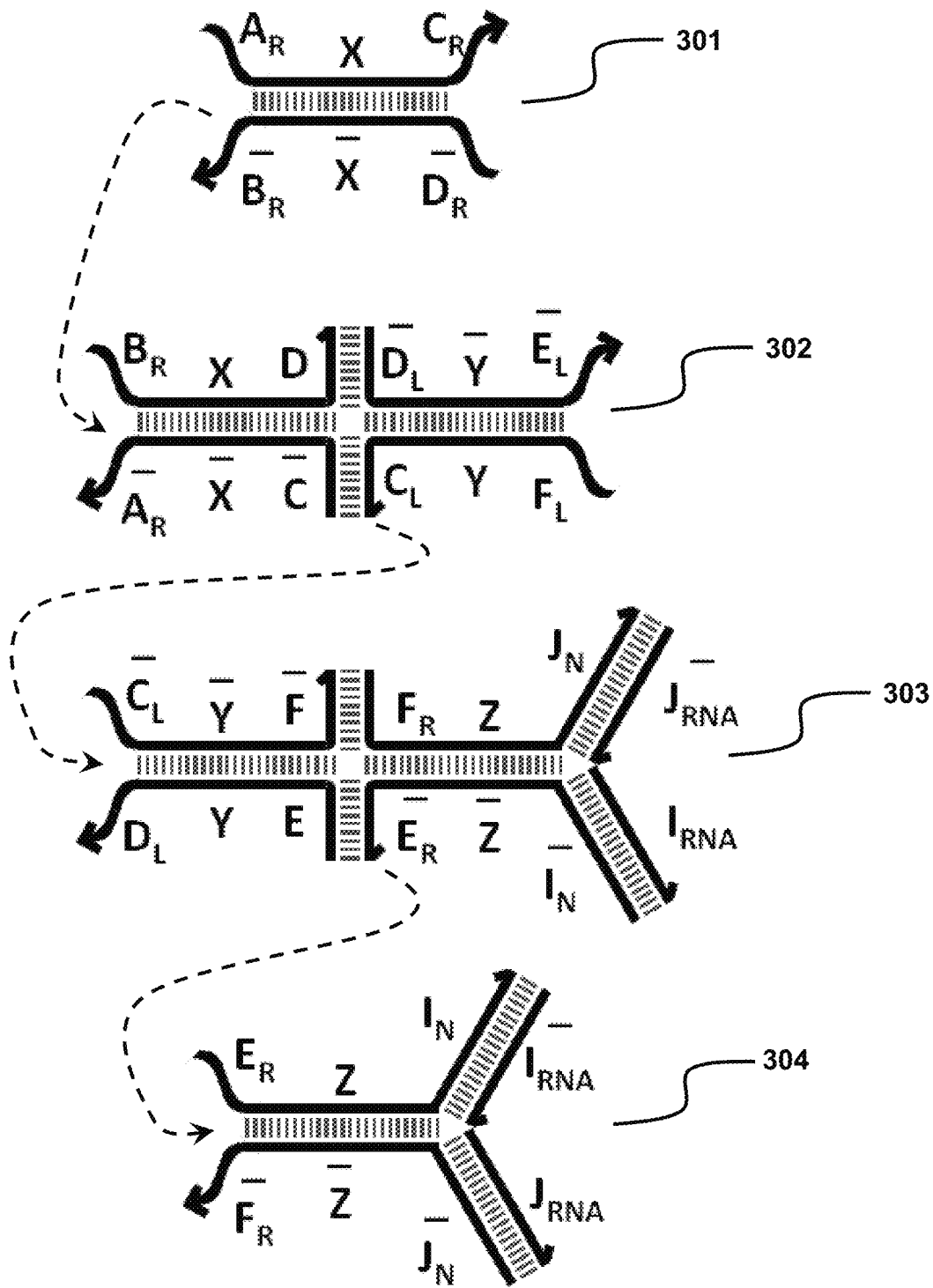
FIG. 11 shows an RNAi adaptor.

In FIG. 11, complex 301 represents a dual toe-hold which can be generated by upstream translators, and can target complex 302 for a strand displacement reaction resulting in the release of a new dual toe-hold that includes the two nucleic acid strands of the distal half of the complex.

Complex 303 is similar to translators 102-104 in FIG. 6A but differs from them by including two RNAi molecules ($\overline{\text{J}}_{RNA}$ and $\text{I}_{RNA}$) that bind to the single strands at the distal (i.e., right hand side as shown in the figure) ends. The other complex (304), on the other hand, resembles a dual toe-hold (e.g., toe-hold 101 in FIG. 6A) but differs by including two RNAi molecules ($\overline{\text{I}}_{RNA}$ and J) at the distal ends.

Therefore, upon release of the distal (i.e., right hand side) half of complex 302 as a new dual toe-hold, the new toe-hold initiates a strand displacement reaction with complex 303, resulting in the release of a complex includes the distal half of the complex along with the RNAi strands. Such a new complex then can initiate a strand displacement reaction with complex 304, leading to release of all of the RNAi molecules ($\overline{\text{J}}_{RNA}$, $\text{I}_{RNA}$, $\overline{\text{I}}_{RNA}$ and J).

Thus, in on embodiment, provided is a composition comprising a first nucleic acid complex comprising (a) a first, a second, a third and a fourth nucleic acid strands each comprising, sequentially, a first, a second and a third fragments and (b) a first and second RNA strands, wherein the first complex comprises: (i) a first duplex region formed between the second fragments of the first and second strands; (ii) a second duplex region formed between the second fragments of the third and fourth strands; (iii) a third duplex region formed between the third fragment of the first strand and the first fragment of the third strand; (iv) a fourth duplex region formed between the first fragment of the second strand and the third fragment of the fourth strand; (v) a fifth duplex region formed between the third fragment of the third strand and the first RNA; and (vi) a sixth duplex region formed between the first fragment of the fourth strand and the second RNA, and the first fragment ($\overline{\text{C}}$) of the first strand and the third fragment (D) of the second strand are single-stranded.

In one aspect, the composition further comprises a second nucleic acid complex comprising a first and a second nucleic acid strands and a first and a second RNA strands, wherein: the second complex comprises a first duplex region formed between the second fragments of the first and second strands, a second duplex region formed between the third fragment of the first strand and the first RNA strand, and a third duplex region formed between the first fragment of the second strand and the second RNA strand, wherein the first fragment (E) of the first strand and the third fragment (F) of the second strand are single-stranded; the third strand of the first complex and the second strand of the second complex have suitable sequence complementarity to allow binding therebetween under hybridizing conditions; and the fourth strand of the first complex and the first strand of the second complex have suitable sequence complementarity to allow binding therebetween under hybridizing conditions.

III. Antisense Adaptor

Figure 12:
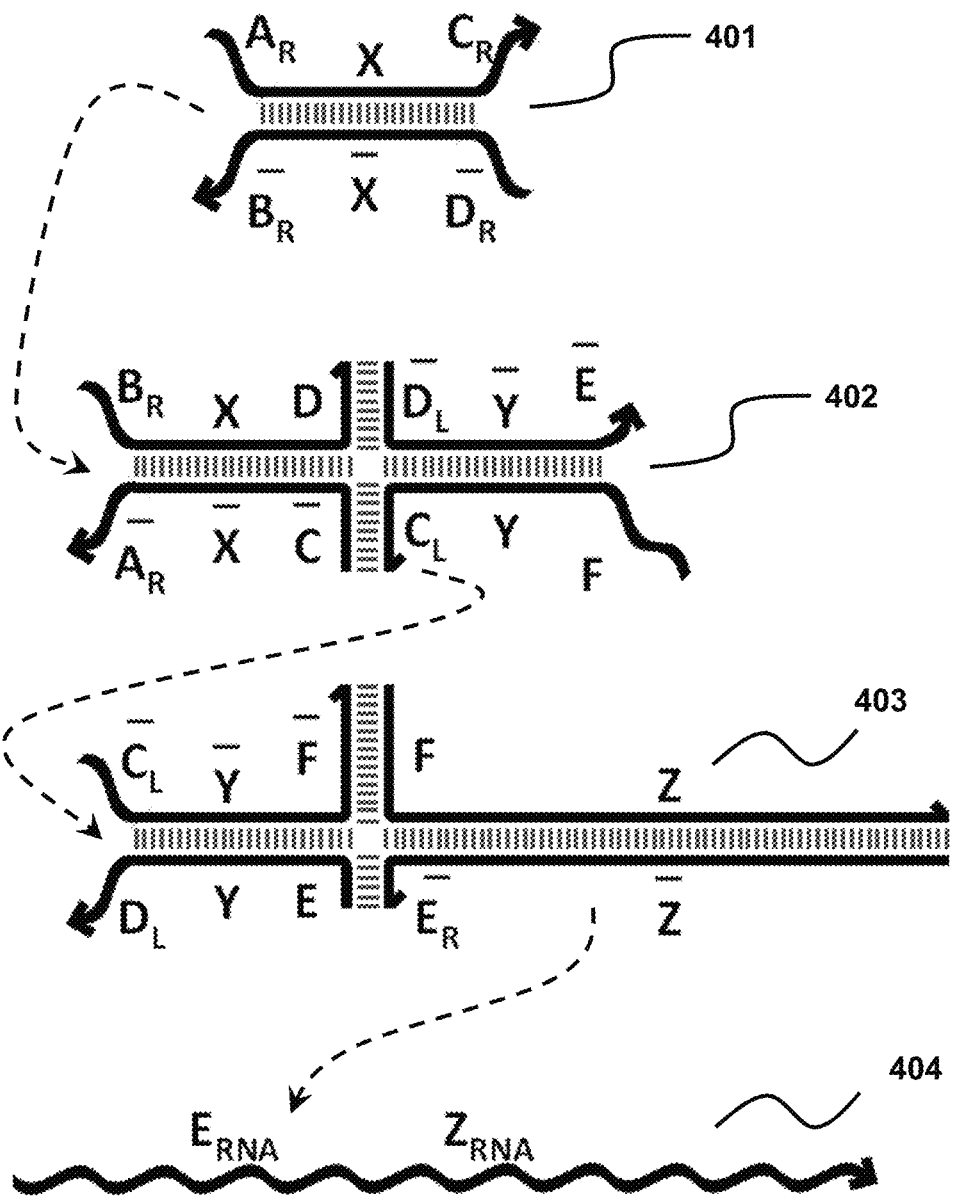
FIG. 12 illustrates an antisense adaptor.

An adaptor also is provided for receiving signals from upstream translators and releasing an antisense RNA. With reference to FIG. 12, complex 401 represents a typical dual toe-hold, as described above, and complex 402 is similar to a typical rotational sequestering translator (e.g., 102-104 of FIG. 6A), except that, optionally, one of the strands has a longer single-stranded region (F). Such a longer single-stranded region (F) is helpful to maintain the stability of translator 403, while allowing the other single-stranded region (E) to be sufficiently short. Likewise, this allows the single-stranded region (E) of translator 402 to be sufficient short to minimize the undesired reaction between translator 402 and the target, 404.

Upon release from the complex 402 by a strand displacement reaction initiated by toe-hold 401, therefore, the distal half of complex (402), which is the new dual toe-hold, targets complex 403 and releases a partial duplex that includes F-Z and $\overline{\text{Z}}$-$\overline{\text{E}}$.

Upon contact with a cellular RNA molecule that includes an E-Z fragment, therefore, the $\overline{\text{Z}}$-$\overline{\text{E}}$ strand is then free to bind to the cellular RNA, undergoing strand displacement and leaving the F-Z strand in solution. The binding between $\overline{\text{Z}}$-$\overline{\text{E}}$ and the cellular RNA can lead to inhibition of activities (e.g., translation and splicing) of the cellular RNA, where the $\overline{\text{Z}}$-$\overline{\text{E}}$ fragment serves as an antisense nucleic acid.

A unique advantage of such a design is that the $\overline{\text{Z}}$-$\overline{\text{E}}$ strand can be quite long. It is known, in an anti-sense application, that the longer the antisense nucleic acid is, the more effective it is at blocking translation. Unfortunately, however, in conventional technologies, longer antisense nucleic acids result in worse off-target effects (e.g., toxicity). This is because such antisense nucleic acids are single stranded. The present disclosure provides an antisense nucleic acid (e.g., the $\overline{\text{Z}}$-$\overline{\text{E}}$ strand) in the form of a partial duplex (i.e., part of the either or both strands are single stranded). Until the antisense nucleic acid binds to the target cellular RNA, therefore, the antisense nucleic acid, even with a great length, only has a small portion exposed in the solution as single stranded. Such reduced exposure, accordingly, reduces the potential off-target effects.

In the present method, therefore, an antisense nucleic acid of a length of greater than, e.g., 30 nt, 35, nt, 40 nt, 45 nt, 50 nt, 55 nt, 60 nt, 65 nt, 70 nt, 80 nt, 90 or 100 nt, can be suitably introduced into a biological system.

Thus, one embodiment provides a composition comprising: (a) a first nucleic acid complex comprising (i) a first nucleic acid strand comprising, sequentially, a first, second and third fragments and defined as B-X-D, (ii) a second nucleic acid strand comprising, sequentially, a first, second and third fragments and defined as $\overline{C}$-$\overline{X}$-$\overline{A}$, (iii) a third strand comprising, sequentially, a first, second and third fragments and defined as $\overline{D}$-$\overline{Y}$-E, and (iv) a fourth strand comprising, sequentially, a first, second and third fragments and defined as F-Y-C, wherein the first complex comprises a first duplex region (X::$\overline{X}$) formed between the second fragments of the first and second strands, a second duplex region ($\overline{Y}$::Y) formed between the second fragments of the third and fourth strands, a third duplex region (D::$\overline{D}$) formed between the third fragment of the first strand and the first fragment of the third strand and a fourth duplex region ($\overline{C}$::C) formed between the first fragment of the second strand and the third fragment of the fourth strand; and (b) a second nucleic acid complex comprising (i) a first nucleic acid strand comprising, sequentially, a first, second and third fragments and defined as $\overline{C}$-$\overline{Y}$-F, (ii) a second nucleic acid strand comprising, sequentially, a first, second and third fragments and defined as E-Y-D, (iii) a third strand comprising, sequentially, a first and second fragments and defined as F-Z, and (iv) a fourth strand comprising, sequentially, a first and second fragment and defined as $\overline{Z}$-$\overline{E}$, wherein the second complex comprises a first duplex region ($\overline{Y}$::Y) formed between the seconds fragments of the first and second strands, a second duplex region (Z::$\overline{Z}$) formed between the second fragment of the third strand and the first fragment of the fourth strand, a third duplex region ($\overline{F}$::F) formed between the third fragment of the first strand and the first fragment of the third strand, and a fourth duplex region (E::$\overline{E}$) formed between the first fragment of the second strand and the second fragment of the fourth strand, wherein the first (B) fragment of the first strand, the third fragment ($\overline{A}$) of the second strand, the third fragment (E) of the third strand, and the first fragment (F) of the fourth strand of the first complex, and the first ($\overline{C}$) fragment of the first strand and the third fragment of the second strand (D) of the second complex are single-stranded; wherein the first, second and third fragments ($\overline{D}$, $\overline{Y}$, and E) of the third strand of the first complex have suitable sequence complementarity to the third, second and first fragments (D, Y, and E) of the second strand of the second complex to allow binding therebetween, under hybridizing conditions, respectively; and wherein the third, second and first fragments (C, Y, and F) of the fourth strand of the first complex have suitable sequence complementarity to the first, second and third fragments ($\overline{C}$, $\overline{Y}$, and F) of the first strand of the second complex to allow binding therebetween, under hybridizing conditions, respectively.

In some aspects, the first fragment (F) of the fourth strand of the first complex is at least 5 nucleotides (nt), or 6 nt, 7 nt, 8 nt, 9 nt, 10 nt, 15 nt, 20 nt longer than the third fragment (E) of the third strand of the first complex. In some aspects, the first fragment (Z) of the fourth strand of the second complex is at least 30 nucleotides (nt), or 35 nt, 40 nt, 45 nt, 50 nt, 55 nt, 60 nt, 65 nt, 70 nt, or 80 nt long.

IV. Fan-In

Figure 13:
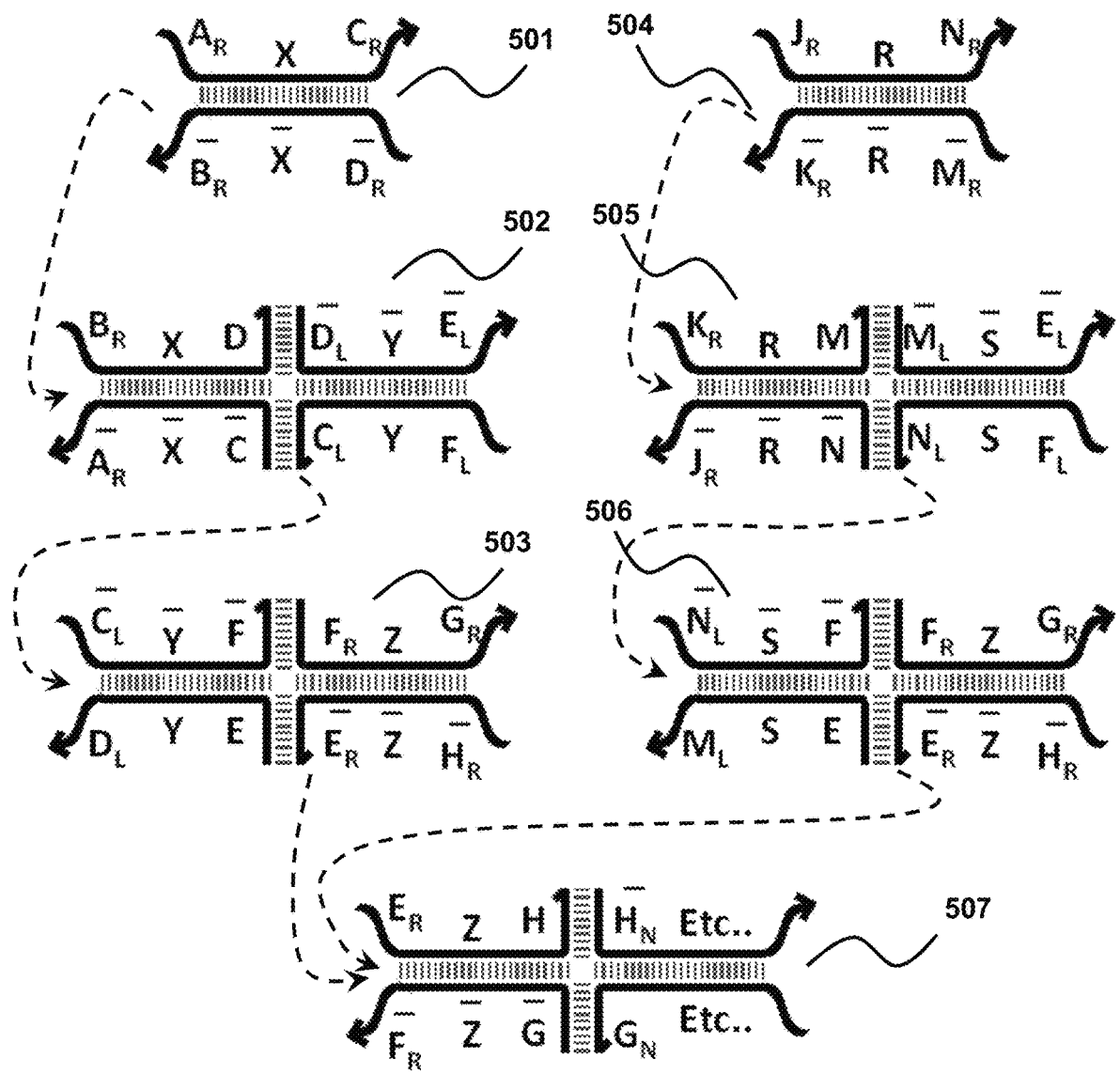
FIG. 13 shows a fan-in translator set.

Also provided is a "fan-in" translator set. A fan-in translator set can take input from two or more different nucleic acids as input signal and produce the same output. In other words, a fan-in translator set can carry out an OR operation. A fan-in set is illustrated in FIG. 13.

In the illustrated fan-in translator set, translators 502-503 and 505-506 are each similar to 102-103 in FIG. 6A and similar to each other. By virtue of their sequence differences, there is no interference between them. Between translators 503 and 506, however, they share the same distal half (F-Z-G/$\overline{H}$-$\overline{Z}$-$\overline{E}$). That means, upon a series strand displacement reactions carried out by their upstream translators, translators 503 and 506 produce the same output toe-hold, that targets complex 507.

Whether the input is toe-hold 501 or 504, therefore, a strand displacement reaction at translator 507 will be triggered.

Accordingly, in one embodiment, provided is a composition comprising a first and a second nucleic acid complexes each comprising a first, a second, a third, and a fourth nucleic acid strands, each of the strands comprising, sequentially, a first, a second and a third fragments, wherein the nucleic acid strands are defined as: B-X-D, $\overline{C}$-$\overline{X}$-$\overline{A}$, $\overline{D}$-$\overline{Y}$-E and F-Y-C for the first, second, third and fourth strands of the first complex, respectively, and $\overline{C}$-$\overline{Y}$-F, E-Y-D, F-Z-G, $\overline{H}$-$\overline{Z}$-$\overline{E}$ for the first, second, third and fourth strands of the second complex, respectively, wherein each letter denotes a fragment and each string of letters connected by "-" denotes a strand, and wherein: each of the first and the second complexes comprises a first duplex region formed between the second fragments of the first and second strands (X::$\overline{X}$ and $\overline{Y}$::Y, in the first and second complexes, respectively), a second duplex region formed between the second fragments of the third and fourth strands (Y::$\overline{Y}$ and Z::$\overline{Z}$), a third duplex region formed between the third fragment of the first strand and the first fragment of the third strand (D::$\overline{D}$ and $\overline{F}$::F), and a fourth duplex region formed between the first fragment of the second strand and the third fragment of the fourth strand ($\overline{C}$::C and E::$\overline{E}$); in each of the first and second complexes, the first fragment (B and $\overline{C}$, in the first and second complexes, respectively) of the first strand, the third fragment ($\overline{A}$ and D) of the second strand, the third fragment (E and G) of the third strand and the first fragment (F and $\overline{H}$) of the fourth strand are single-stranded; the third strand of the first complex ($\overline{D}$-$\overline{Y}$-E) has suitable sequence complementarity to the second strand of the second complex (E-Y-D) to allow binding therebetween under hybridizing conditions; and the fourth strand of the first complex (F-Y-C) has suitable sequence complementarity to the first strand of the second complex ($\overline{C}$-$\overline{Y}$-F) to allow binding therebetween under hybridizing conditions; further comprising a third nucleic acid complex comprising a first and a second nucleic acid strands, each of the strands comprising, sequentially, a first, a second and a third fragments, wherein the first and second strands are defined as E-Z-H and $\overline{G}$-$\overline{Z}$-$\overline{F}$ respectively, wherein the third nucleic acid complex comprises a duplex region formed between the second fragments of the first and second strands (Z::$\overline{Z}$) and the first fragment (E) of the first strand and the third fragment of the second strand ($\overline{F}$) are singled-stranded, and wherein: the third strand of the second complex (F-Z-G) has suitable sequence complementarity to the second strand of the third complex ($\overline{G}$-$\overline{Z}$-$\overline{F}$) to allow binding therebetween under hybridizing conditions; and the fourth strand of the second complex ($\overline{H}$-$\overline{Z}$-$\overline{E}$) has suitable sequence complementarity to the first strand of the third complex (E-Z-H) to allow binding therebetween under hybridizing conditions; and yet further comprising a fourth and a fifth nucleic acid complexes, each complex comprising a first, a second, a third and a fourth nucleic acid strands, each of which strands comprises, sequentially, a first, a second and a third fragments, wherein the strands are defined as: K-R-M, $\overline{\text{N}}$-$\overline{\text{R}}$-J, $\overline{\text{M}}$-$\overline{\text{S}}$-$\overline{\text{E}}$ and F-S-N for the first, second, third and fourth strands of the fourth complex, respectively; and $\overline{\text{N}}$-$\overline{\text{S}}$-F, E-S-M, F-Z-G and $\overline{\text{H}}$-$\overline{\text{Z}}$-$\overline{\text{E}}$ for the first, second, third and fourth strands of the fifth complex, respectively, wherein: each of the fourth and the fifth complexes comprises a first duplex region formed between the second fragments of the first and second strands (R::$\overline{\text{R}}$ and $\overline{\text{S}}$::S, in the fourth and fifth complexes, respectively), a second duplex region formed between the second fragments of the third and fourth strands ($\overline{\text{S}}$::S and Z::$\overline{\text{Z}}$), a third duplex region formed between the third fragment of the first strand and the first fragment of the third strand (M::$\overline{\text{M}}$ and $\overline{\text{F}}$::F), and a fourth duplex region formed between the first fragment of the second strand and the third fragment of the fourth strand ($\overline{\text{N}}$::N and E::$\overline{\text{E}}$); in each of the fourth and fifth complexes, the first fragment (K and $\overline{\text{N}}$, in the first and second complexes, respectively) of the first strand, the third fragment (J and M) of the second strand, the third fragment ($\overline{\text{E}}$ and G) of the third strand and the first fragment (F and $\overline{\text{H}}$) of the fourth strand are single-stranded; the third strand of the fourth complex ($\overline{\text{M}}$-$\overline{\text{S}}$-$\overline{\text{E}}$) has suitable sequence complementarity to the second strand of the fifth complex (E-S-M) to allow binding therebetween under hybridizing conditions; the fourth strand of the fourth complex (F-S-N) has suitable sequence complementarity to the first strand of the fifth complex ($\overline{\text{N}}$-$\overline{\text{S}}$-F) to allow binding therebetween under hybridizing conditions; the third strand of the second complex (F-Z-G) and the third strand of the fifth complex (F-Z-G) have suitable sequence identity to allow them to bind to a same target nucleic acid under hybridizing conditions; and the fourth strand of the second complex ($\overline{\text{H}}$-$\overline{\text{Z}}$-$\overline{\text{E}}$) and the fourth strand of the fifth complex ($\overline{\text{H}}$-$\overline{\text{Z}}$-$\overline{\text{E}}$) have suitable sequence identity to allow them to bind to a same target nucleic acid under hybridizing conditions.

V. Fan-Out

Opposite to a fan-in translator set, a "fan-out" translator set takes a single input and produce multiple output nucleic acids. In one aspect, the multiple output nucleic acids have difference sequences so that they can carry out different functions or downstream reactions. In another aspect, the multiple output nucleic acids are identical and thus the fan-out translator set serves as an amplifier.

Figure 14A:
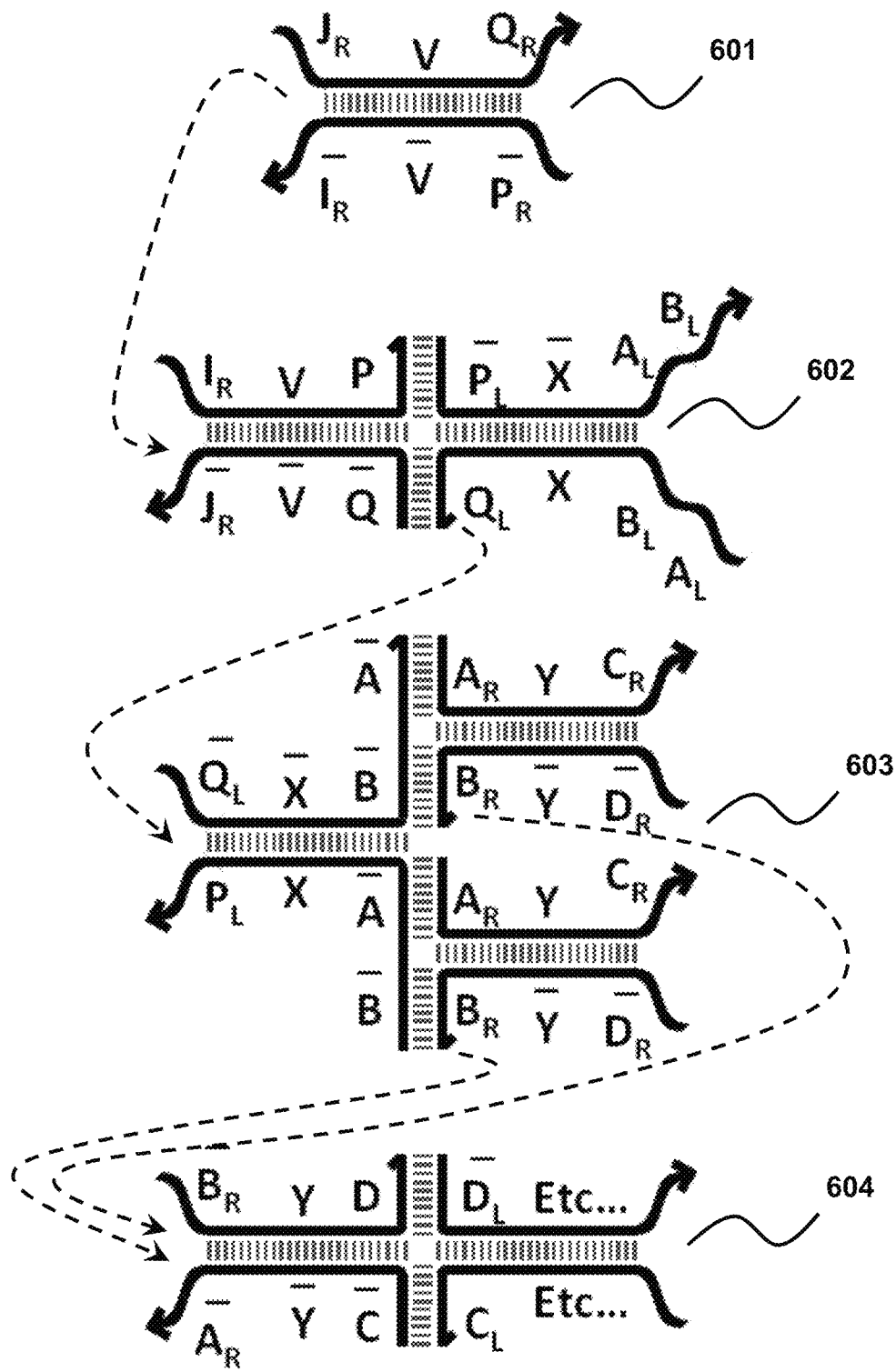
FIG. 14A-14D depict four fan-out translator sets. Two of these sets produce two or more identical translators, thus working as amplifiers (A and B), while the other two sets generate two or more different downstream translators (C and D)

FIG. 14A illustrates a fan-out translator set that takes one toe-hold as input and produces two identical new toe-holds. Similarly, the fan-out set in FIG. 14B produces four identical new toe-holds. FIG. 14C-D, on the other hand, presents fan-out translator sets that generate two or more different new toe-holds.

In FIG. 14A, nucleic acid 601 is a typical dual toe-hold as described herein. Complex 602 differs from translators 102 and 103 of FIG. 6A on that the single-stranded regions on the distal end are longer, containing two, rather than one, consecutive fragments. As apparent in complex 603, each set of the consecutive fragments (A-B) is capable of releasing a new toe-hold which, upon such release, has two separate single-stranded regions, A and B, on two separate strands. Either one of these new toe-holds can initiate a new strand displacement reaction with translator 604, therefore.

Figure 14B:
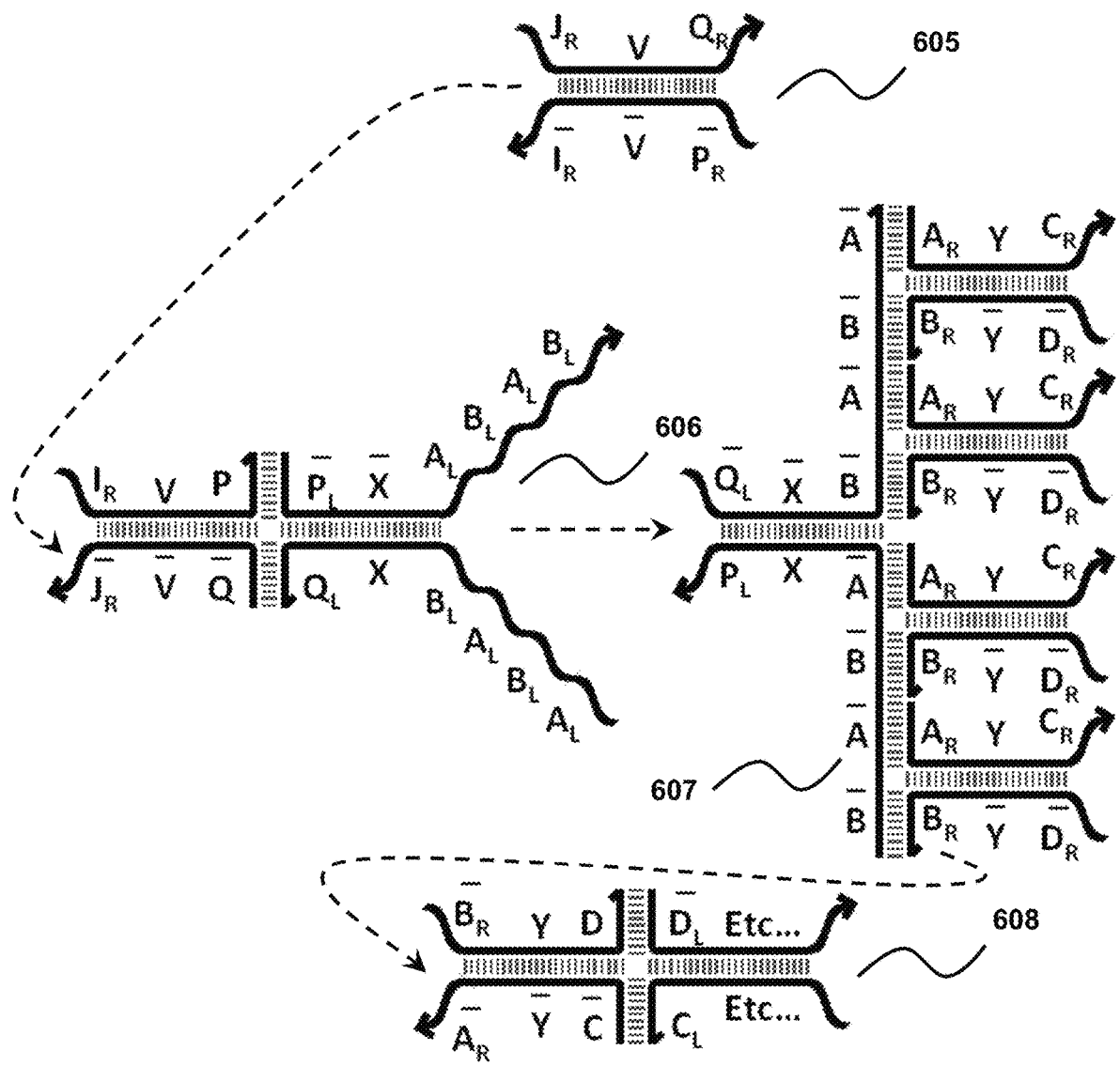
Figure 14C:
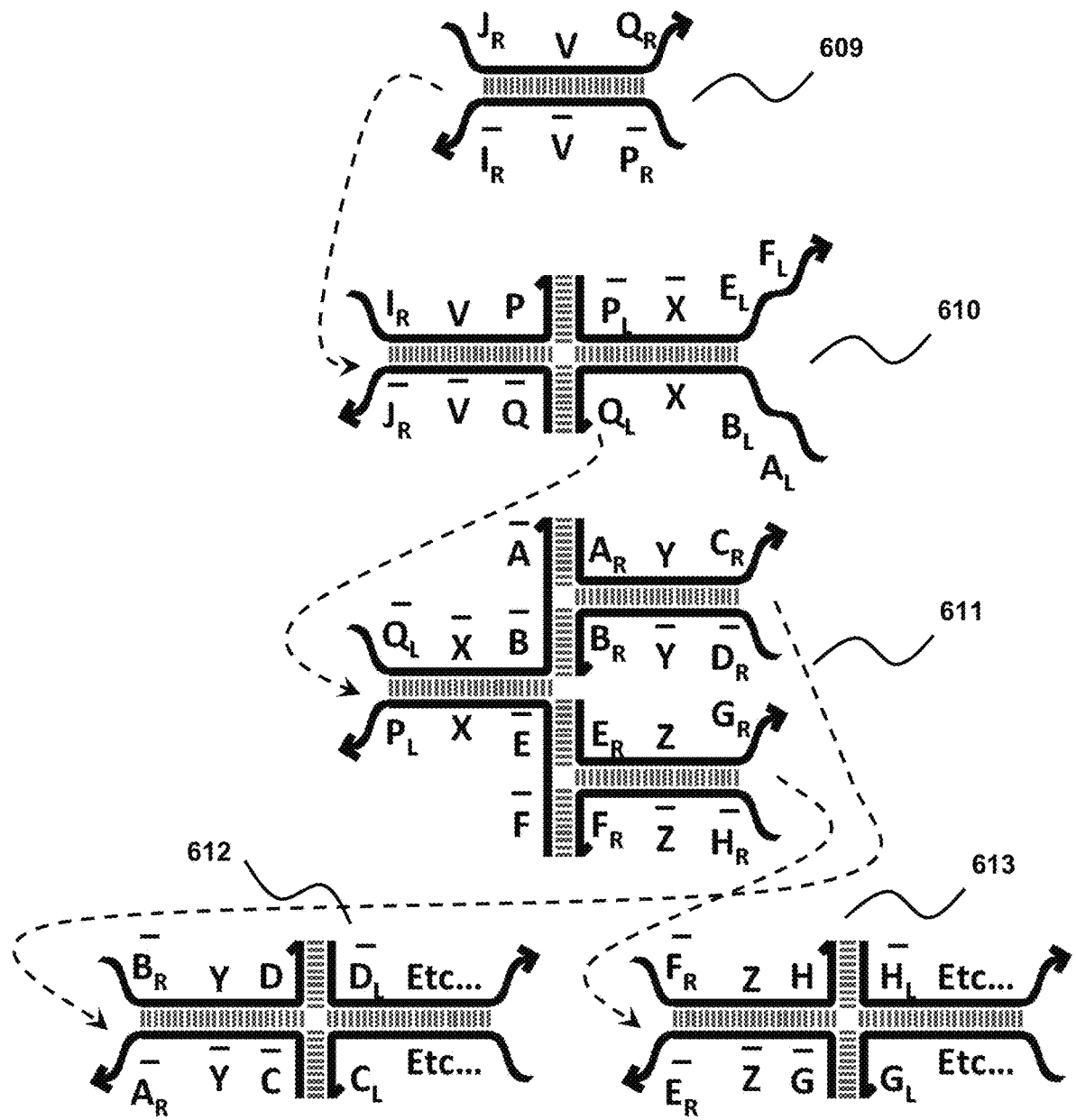
Figure 14D:
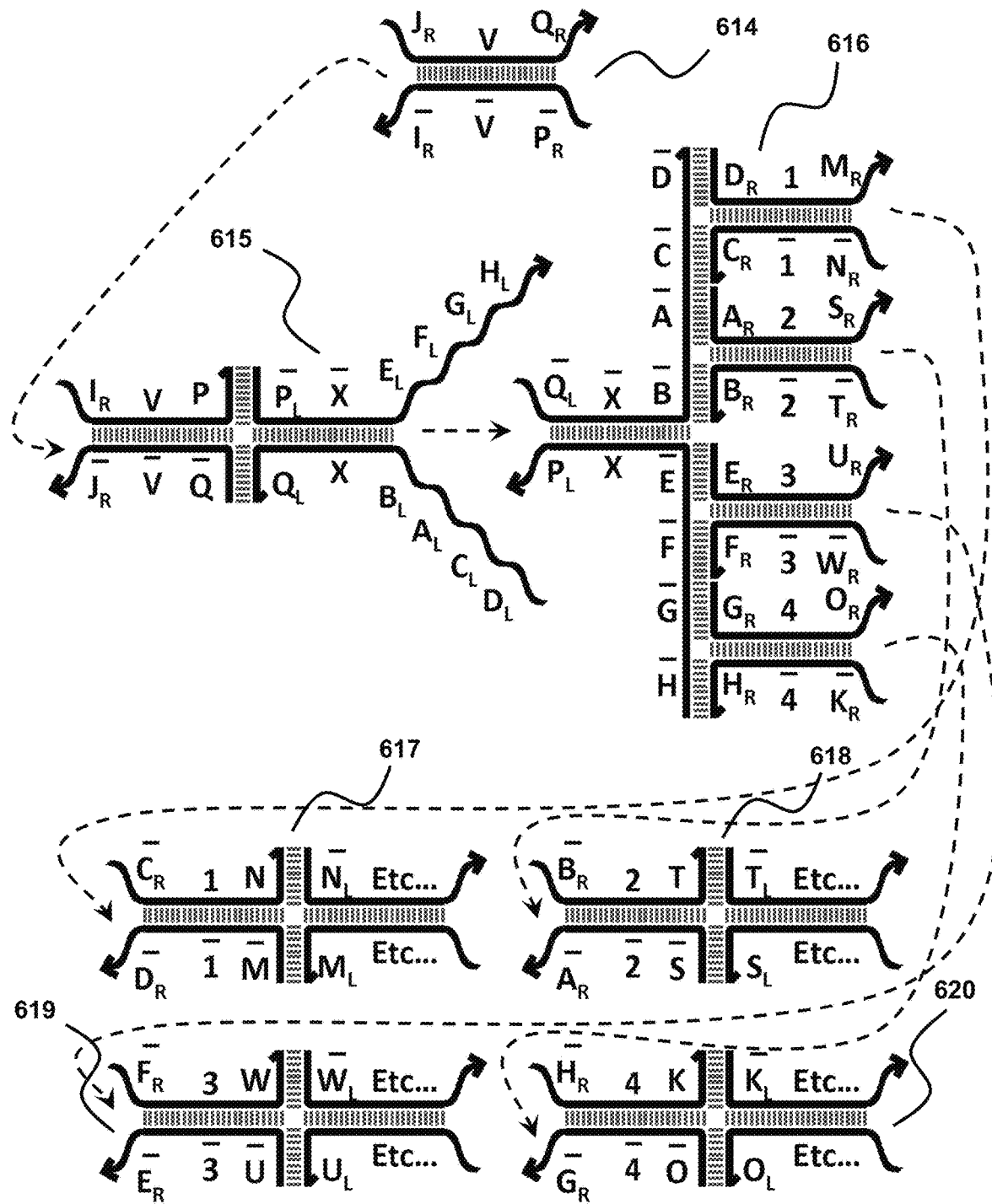

The translators in FIG. 14B are similar to those of FIG. 14A (e.g., toe-hold 605 is similar to toe-hold 601 and translator 608 is similar to translator 604), except that the single-stranded regions in translator 606 each has four consecutive fragments capable of releasing two new toe-holds when reacting with translator 607.

The translator set in FIG. 14C can take the same toe-hold input (609) as that of FIG. 14A-B (601 and 605) but the translator 610 releases a toe-hold, upon contact with the input, that is different from FIG. 14A-B. Such a difference is more apparent, as reflected in the corresponding strands in translator 611. That is, upon contact with the released toe-hold from translator 610 and strand displacement reactions, translator 611 releases two different toe-holds. One of these two toe-holds is capable of initiating a new strand displacement reaction with translator 612, and the other with translator 613. Thus, the translator set in FIG. 14B is capable of generating, from the input of one toe-hold (609), two different new toe-hold outputs, from translators 612 and 613, respectively.

Similar to the translator set in FIG. 14C, the translator set of FIG. 14D, including translators 615 and 616, also can take one toe-hold (614) as input and produce four different new toe-holds as outputs, each released from translators 617-620, respectively.

One embodiment of the disclosure, therefore, provides a nucleic acid complex comprising a first, a second, a third, a fourth, a fifth and a sixth nucleic acid strands, wherein: the first strand comprises, sequentially, a first, a second, a third and a fourth fragments and is defined as $\overline{\text{Q}}$-$\overline{\text{X}}$-$\overline{\text{B}}$-$\overline{\text{A}}$, wherein each letter denotes a fragment and a string of letters connected by "-" denotes a strand; the second strand comprises, sequentially, a first, a second, a third and a fourth fragments and is defined as $\overline{\text{B}}$-$\overline{\text{A}}$-$\overline{\text{X}}$-P; the third and fifth strands each comprises, sequentially, a first, a second and a third fragments and is defined as A-Y-C; and the fourth and sixth strands each comprises, sequentially, a first, a second and a third fragments and is defined as $\overline{\text{D}}$-$\overline{\text{Y}}$-B; and wherein the complex comprises: a first duplex region ($\overline{\text{X}}$:X) formed between the second fragment of the first strand and the thirdstrand of the second strand; a second duplex region (A::A) formed between the fourth fragment of the first strand and the first strand of the third strand; a third duplex region ($\overline{\text{B}}$::B) formed between the third fragment of the first strand and the third fragment of the fourth strand; a fourth duplex region ($\overline{\text{A}}$::A) formed between the second fragment of the second strand and the first fragment of the fifth strand; a fifth duplex region ($\overline{\text{B}}$::B) formed between the first fragment of the second strand and the third fragment of the sixth strand; a sixth duplex region (Y::$\overline{\text{Y}}$) formed between the second fragments of the third and fourth strands; and a seventh duplex region (Y::$\overline{\text{Y}}$) formed between the second fragments of the fifth and sixth strands, and wherein the first fragment ($\overline{\text{Q}}$) of the first strand, the fourth fragment (P) of the second strand, the third fragments (C) of the third and fifth strands and the first fragments ($\overline{\text{D}}$) of the fourth and sixth strands are single-stranded.

Likewise, a nucleic acid complex that fans out two or more different toe-holds is also provided.

VI. Compound Conditional

A "compound conditional" translator set carries out an AND operation. A compound conditional set requires two separate input signals to activate and release an output nucleic acid.

Figure 15:
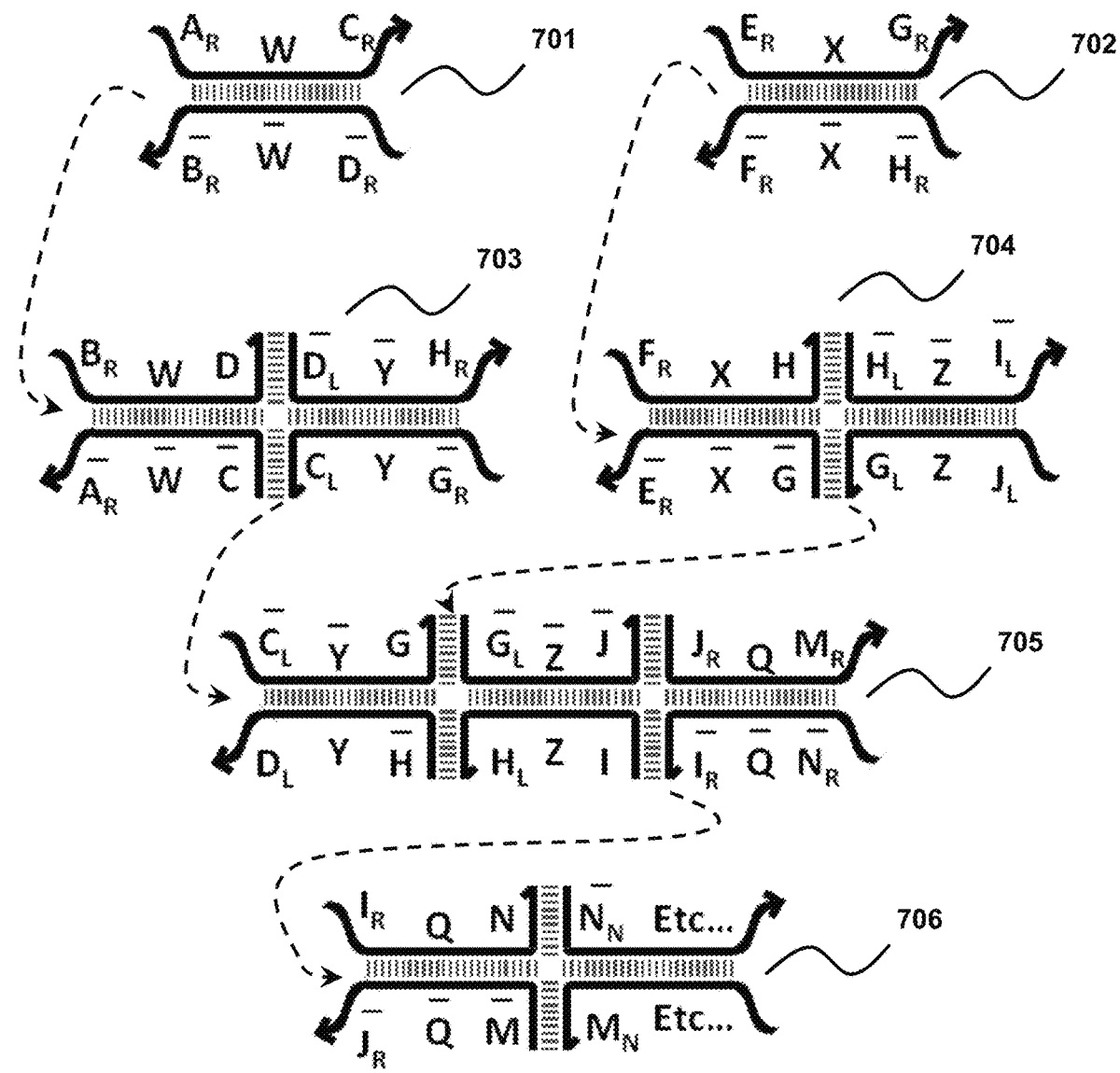
FIG. 15 illustrates a compound conditional translator set.

FIG. 15 illustrates a compound conditional translator set, which includes at least three translator nucleic acid complexes 703, 704 and 705. Translator 703 takes toe-hold 701 as input and produces a first new toe-hold containing the distal half of 703. Likewise, translator 704 takes toe-hold 702 as input and produces a second new toe-hold containing the distal half of 704.

Translator 705 contains at least six strands comprised, from left to right, of three duplex pairs. Only upon contact with the first new toe-hold released from translator 703, can translator 705 undergo a strand displacement reaction, resulting in exposure of two single-stranded regions (G and H) of the middle duplex.

Subsequently, upon contact with the second new toe-hold produced by translator 704, another strand displacement reaction occurs and releases the third duplex pair of 705 as a third new toe-hold. This third new toe-hold then can optionally trigger further reactions through translator 706, for instance.

Thus, in one embodiment, provided is a composition comprising a first, a second and a third nucleic acid complexes, wherein: the first complex comprises a first, a second, a third and a fourth nucleic acid strands each comprising, sequentially, a first, a second and a third fragments and defined as B-W-D, $\overline{C}$-$\overline{W}$-$\overline{A}$, $\overline{D}$-$\overline{Y}$-H, and $\overline{G}$-Y-C, respectively, wherein each letter denotes a fragment and each string of letters connected by "-" denotes a strand, and wherein the first complex comprises a first duplex region (W::$\overline{W}$) formed between the second fragments of the first and second strands, a second duplex region ($\overline{Y}$::Y) formed between the second fragments of the third and fourth strands, a third duplex region (D::$\overline{D}$) formed between the third fragment of the first strand and the first fragment of the third strand; and a fourth duplex region ($\overline{C}$::C) formed between the first fragment of the second strand and the third fragment of the fourth strand; the second complex comprises a first, a second, a third and a fourth nucleic acid strands each comprising, sequentially, a first, a second and a third fragments and defined as F-X-H, $\overline{G}$-$\overline{X}$-E, $\overline{H}$-$\overline{Z}$-$\overline{I}$ and J-Z-G, respectively, wherein the second complex comprises a first duplex region (X::$\overline{X}$) formed between the second fragments of the first and second strands, a second duplex region ($\overline{Z}$::Z) formed between the second fragments of the third and fourth strands, a third duplex region (H::$\overline{H}$) formed between the third fragment of the first strand and the first fragment of the third strand; and a fourth duplex region ($\overline{G}$::G) formed between the first fragment of the second strand and the third fragment of the fourth strand; the third complex comprises a first, a second, a third, a fourth, a fifth and a sixth nucleic acid strands each comprising, sequentially, a first, a second and a third fragments and defined as $\overline{C}$-$\overline{Y}$-G, $\overline{H}$-Y-D, $\overline{G}$-$\overline{Z}$-$\overline{J}$, I-Z-H, J-Q-M and $\overline{N}$-$\overline{Q}$-$\overline{I}$, respectively, wherein the third complex comprises a first duplex region ($\overline{Y}$::Y) formed between the second fragments of the first and second strands, a second duplex region ($\overline{Z}$::Z) formed between the second fragments of the third and fourth strands, a third duplex region (Q::$\overline{Q}$) formed between the second fragments of the fifth and sixth strands, a fourth duplex region (G::$\overline{G}$) formed between the third fragment of the first strand and the first fragment of the third strand; a fifth duplex region ($\overline{H}$::H) formed between the first fragment of the second strand and the third fragment of the fourth strand, a sixth duplex region ($\overline{J}$::J) formed between the third fragment of the third strand and the first fragment of the fifth strand, and a seventh duplex region (I::$\overline{I}$) formed between the first fragment of the fourth strand and the third fragment of the sixth strand; wherein, in the first complex, the first fragment (B) of the first strand, the third fragment ($\overline{A}$) of the second fragment, the third fragment (H) of the third strand, and the first fragment ($\overline{G}$) of the fourth strand are single-stranded; in the second complex, the first fragment (F) of the first strand, the third fragment ($\overline{E}$) of the second fragment, the third fragment ($\overline{I}$) of the third strand, and the first fragment (J) of the fourth strand are single-stranded; and in the third complex, the first fragment ($\overline{C}$) of the first strand, the third (D) fragment of the second strand, the third fragment (M) of the fifth fragment, and the first fragment ($\overline{N}$) of the sixth strand are single-stranded, and wherein: the third strand ($\overline{D}$-$\overline{Y}$-H) of the first complex and the second strand ($\overline{H}$-Y-D) of the third complex have suitable sequence complementarity to allow binding therebetween under hybridizing conditions; the fourth strand ($\overline{G}$-Y-C) of the first complex and the first strand ($\overline{C}$-$\overline{Y}$-G,) of the third complex have suitable sequence complementarity to allow binding therebetween under hybridizing conditions; the third strand ($\overline{H}$-$\overline{Z}$-$\overline{I}$) of the second complex and the fourth strand (I-Z-H) of the third complex have suitable sequence complementarity to allow binding therebetween under hybridizing conditions; and the fourth strand (J-Z-G) of the second complex and the third strand ($\overline{G}$-$\overline{Z}$-$\overline{J}$) of the third complex have suitable sequence complementarity to allow binding therebetween under hybridizing conditions.

VII. Inverter

An "inverter" constitutes one or more translators which, upon contact with an input signal, produce a nucleic acid ("stopper") that blocks a strand displacement reaction that otherwise would take place upon initiation by a different input signal in the system.

Figure 16:
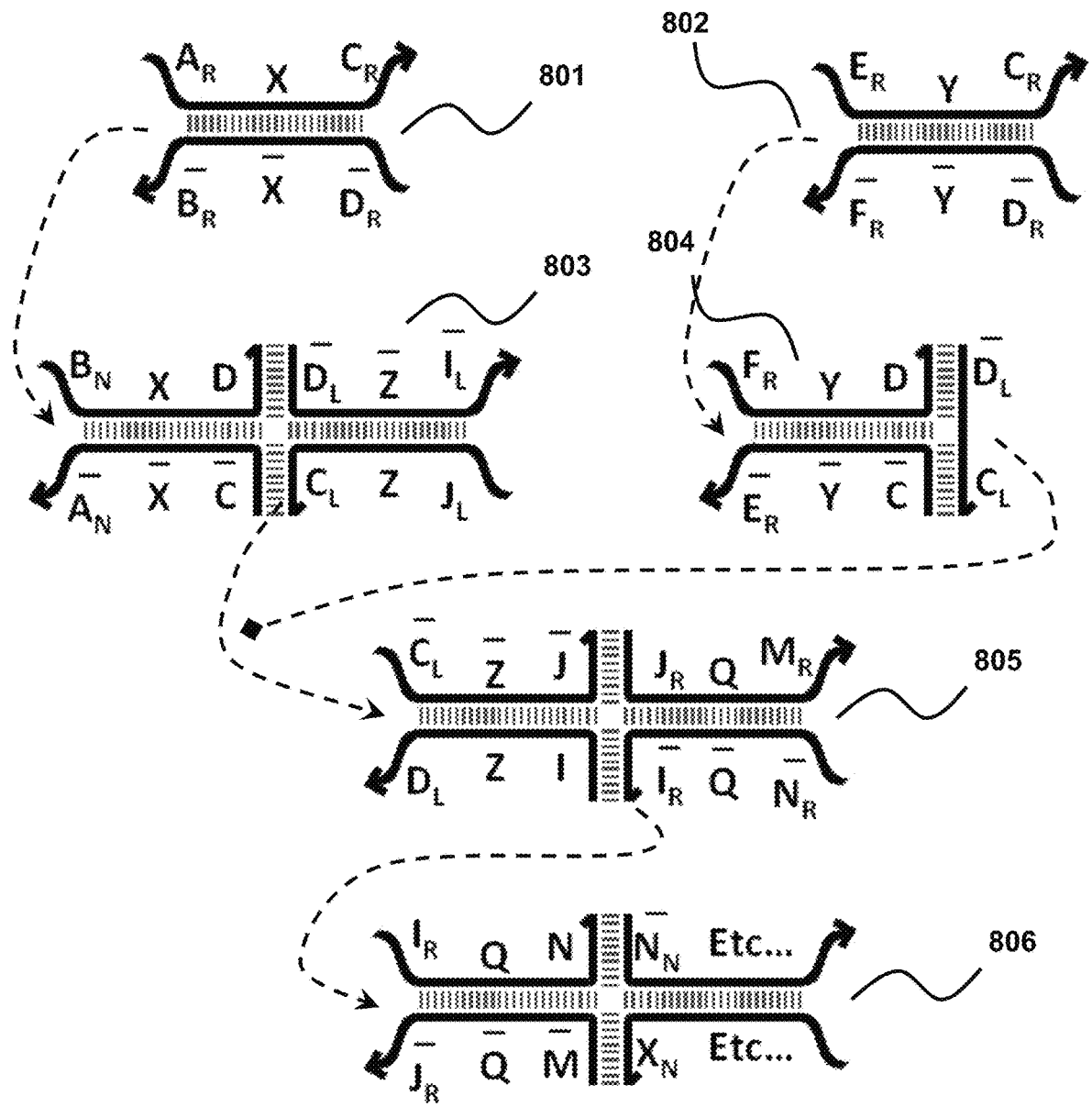
FIG. 16 shows an inverter.

As illustrated in FIG. 16, the inverter nucleic complex 804 is comprised of three strands, two of which, F-Y-D and $\overline{C}$-$\overline{Y}$-E, form a duplex region between the middle fragments (Y::$\overline{Y}$). The third strand includes two fragments, C and $\overline{D}$, each complementary to one fragment of the other two strands. Upon contact with toe-hold 802, a strand displacement reaction would take place, leading to release of the third strand, C-$\overline{D}$.

Nucleic acid complex 803 is a translator that takes toe-hold 801 as input and produces the distal half of the complex, a new toe-hold, as output. This new toe-hold, if in contact with translator 805, can carry out a subsequent strand displacement reaction, with potential subsequence reaction with translator 806.

The signal processing route of 801-803-805-806 cannot happen, however, if toe-hold 802 comes into contact with inverter 804 and releases the stopper strand C-$\overline{D}$ before the strand displacement between toe-hold 801 and translator 803 occurs. This is so because the stopper strand C-$\overline{D}$ binds to the exposed single-stranded regions, $\overline{C}$ and D, thereby blocking the strand displacement reaction between 805 and the toe-hold produced from translator 803.

Provided in embodiment, therefore, is a composition comprising a first and a second nucleic complexes, wherein: the first complex comprises a first, a second, a third and a fourth nucleic acid strands each comprising, sequentially, a first, a second and a third fragments and defined as B-X-D, $\overline{C}$-$\overline{X}$-$\overline{A}$, $\overline{D}$-$\overline{Z}$-$\overline{I}$ and J-Z-C, respectively, wherein each letter denotes a fragment and each string of letters connected by "-" denotes a strand, and wherein the first complex comprises a first duplex region (X::$\overline{X}$) formed between the second fragments of the first and second strands, a second duplex region ($\overline{Z}$::Z) formed between the second fragments of the third and fourth strands, a third duplex region (D::$\overline{D}$) formed between the third fragment of the first strand and the first fragment of the third strand, and fourth duplex region ($\overline{C}$::C) formed between the first fragment of the second strand and the third fragment of the fourth strand; and the second complex comprises a first and second nucleic acid strands each comprising, sequentially, a first, a second and a third fragment and defined as F-Y-D and $\overline{C}$-$\overline{Y}$-E, respectively, and a third nucleic acid comprising, sequentially, a first and a second fragment and defined as $\overline{D}$-C, wherein the second complex comprises a first duplex region (Y::$\overline{Y}$) formed between the second fragments of the first and second strand, a second duplex region (D::D̄) formed between the third fragment of the first strand and the first fragment of the third strand, and a third duplex region (C̄::C) formed between the first fragment of the second strand and the second fragment of the third strand; wherein the first fragment (B) of the first strand of the first complex, the third fragment (Ā) of the second strand of the first complex, the third fragment (I) of the third strand of the first complex, the first fragment (J) of the fourth strand of the first complex, the first fragment (F) of the first strand of the second complex, and the third fragment (E) of the second strand of the second complex are single-stranded; and wherein: the third strand (D̄-C) of the second complex and the combination of the first fragment (D̄) of the third strand of the first complex and the third fragment (C) of the fourth strand of the first complex, sequentially, have suitable sequence identity to allow their binding to a same target nucleic acid sequence.

For any of the above translators and translator sets, it is contemplated that chemical modifications can be used to reduce or eliminate toe-hold clashing, that is, unintended binding between toe-holds and single-stranded regions of any translators in a system, such as a cell. Such modifications can easily be designed with information provided in the disclosure. Further, for each translator set, the corresponding illustrative figure provides exemplary modifications, as annotated by subscripts N, R, and L. The desired properties of such modifications are provided in Table 2.

In some aspects, it is noted that nucleic acid fragments, if not specifically designated as a part of a duplex region, are meant to be single-stranded. Indication of single-strandedness is also apparent in the accompanying figures.

The length of each nucleic acid strand or fragment can be determined computationally or experimentally. Table 1 illustrates the influence of such length, in particular for toe-holds. In one aspect, each of the fragments is from about 3 bases to about 50 bases long. Alternatively, the fragments, are at least about 3, 4, 5, 6, 7, 8, 9, 10, 11 or 12 bases long. In another aspect, the fragments are not longer than about 50, 45, 40, 35, 30, 29, 28, 27, 26, 25, 24, 23, 22, 21, 20, 19, 28, 17, 16, 15, 14, 13, 12, 11, 10, 9, 8, 7, 6, or 5 bases. Also, fragments that exists in single-stranded forms, such as the toe-holds, can be relatively shorter, such as between about 3, 4, 5, 6, 7, 8, 9, 10 bases and about 30, 29, 28, 27, 26, 25, 24, 23, 22, 21, 20, 19, 28, 17, 16, or 15 bases. In one aspect, a toe-hold fragment is at least about 3, 4, 5, 6, 7, 8, 9, 10, 11 or 12 bases long. In another aspect, a toe-hold fragment is not longer than about 20, 19, 28, 17, 16, 15, 14, 13, 12, 11, 10, 9, 8, 7, 6, or 5 bases. By contrast, the fragments that form duplex regions within a translator can be relatively longer.

Methods and Computer Modeling

The present disclosure further provides methods of using translators of the present disclosure to conduct computation and, in particular, propagate information in a biological environment. For instance, an mRNA adaptor can be used to detect the presence of a pathogenic or neoplastic nucleic acid and produces an output signal in the form of, e.g., a toe-hold. If necessary, multiple mRNA adaptors can be used having specificity to multiple nucleic acids to ensure reliable detection.

Other translators in the system, such as fan-in, fan-out, and inverter translators, then can be used to process the signals generated by the mRNA adaptors, leading eventually to productions of regulatory nucleic acids, e.g., RNAi and antisense RNA, with the corresponding RNAi and antisense adaptor. By virtue of carefully tailored processing, the exact sequences and amounts of these regulatory RNA can be controlled with precision. Accordingly, biological reactions such as apoptosis and immune response can be triggered by these regulatory RNA, bringing about therapeutic or diagnostic benefits.

It would be appreciated readily that the translators, compositions, and systems described here can include biological materials, but they also can be modeled mathematically with a computer. Accordingly, the present disclosure also provides computer methods, systems, and program code-embedded media for carrying out such modeling.

Corresponding to each translator, composition or system in the present disclosure, therefore, a computer-implemented method is provided in which the computer is configured to represent their sequence, structure, synthesis, and strand displacement reaction.

The methodology described here can be implemented on a computer system or network. A suitable computer system can include at least a processor and memory; optionally, a computer-readable medium that stores computer code for execution by the processor. Once the code is executed, the computer system carries out the described methodology.

In this regard, a "processor" is an electronic circuit that can execute computer programs. Suitable processors are exemplified by but are not limited to central processing units, microprocessors, graphics processing units, physics processing units, digital signal processors, network processors, front end processors, coprocessors, data processors and audio processors. The term "memory" connotes an electrical device that stores data for retrieval. In one aspect, therefore, a suitable memory is a computer unit that preserves data and assists computation. More generally, suitable methods and devices for providing the requisite network data transmission are known.

Also contemplated is a non-transitory computer readable medium that includes executable code for carrying out the described methodology. In certain embodiments the medium further contains data or databases needed for such methodology.

EXAMPLE

The present disclosure is further illustrated by reference to this example, which presents the results of kinetic simulation of the time course behavior of Rotationally Sequestered Translator (RST) networks of the present disclosure, as compared side by side to kinetic simulations of the Toe-Hold Sequestered Translator (THST) networks, mentioned above under the subsection heading "Toe-Hold Sequestering," with reference to FIG. 2 and FIG. 3.

Mechanisms were generated that included series of N translations, referred to as "the number of stages," which derive their forward rate constants from Frezza, B. M., ORCHESTRATION OF MOLECULAR INFORMATION THROUGH HIGHER ORDER CHEMICAL RECOGNITION: A THESIS PRESENTED, The Scripps Research Institute, La Jolla, California (2010), at Chapter 3. The mechanisms include as well background "leak" of the translators, also with rate constants per Frezza (2010), and "clashing" interactions. These latter derive their rate constants from the nearest neighbor free energy of binding, see Allawi and SantaLucia, *Biochemistry* 36: 10581-94 (1997), using the standard forward rate constant for hybridization ($10^5$ per molar per second) and the detailed balance to derive the backwards rate constant.

For each simulation, foreground signal and background signal simulations were conducted for both networks of RSTs and THSTs. "Foreground signal" refers to the concentration of final output sequence generated, given initial input sequence at equal concentration to the other translators in the simulation. "Background signal" denotes the concentration of final output sequence generated, given no initial input sequence.

These simulations demonstrate the idealized response each network design should provide under conditions of varying toe-old length, concentration of the translators, and size of the network (number of stages).

Figure 17M:
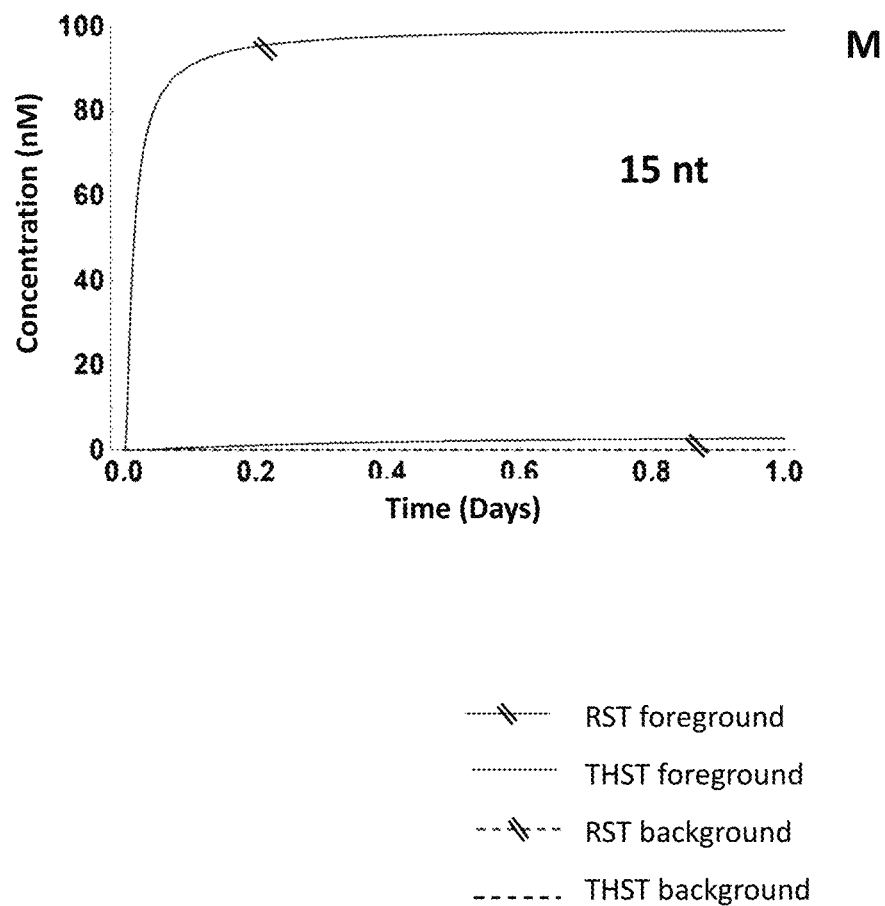
Figure 18D:
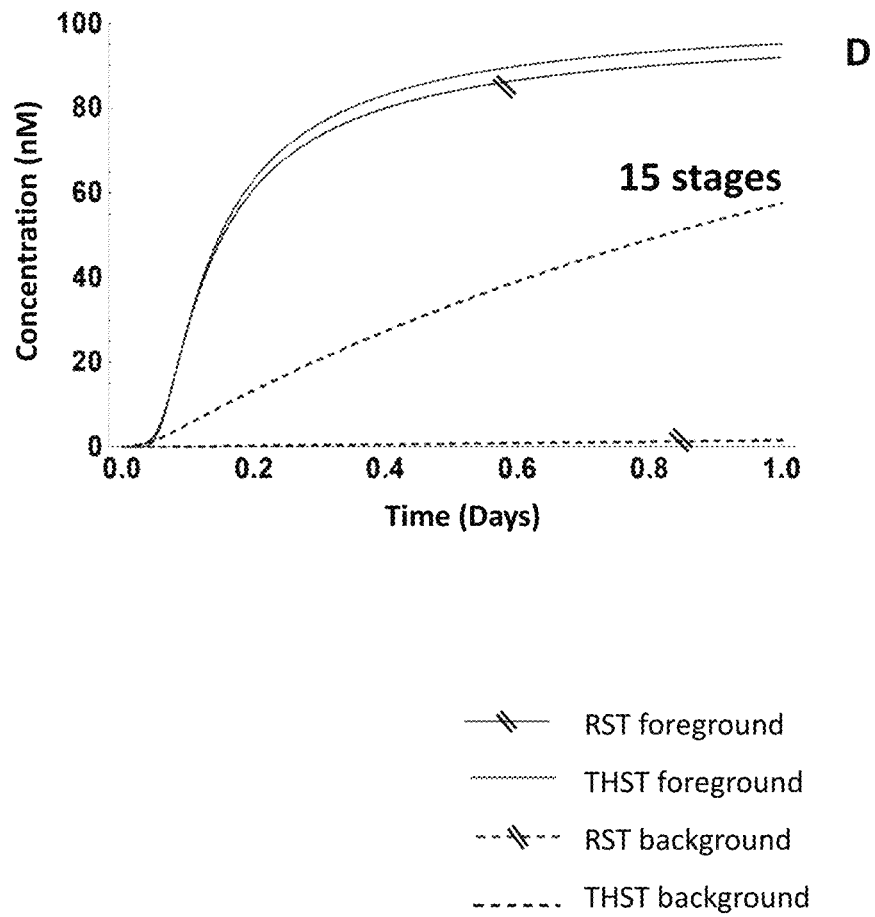

FIG. 17A-M depicts the simulation results for RST and THST, with respect both to foreground signal and to background signal for different sizes of the toe-holds, ranging from 3 to 15 nucleotides (nt). All simulations were conducted with 100 nM translators for three stages. FIG. 17 shows that, at extremely short toe-holds, RSTs in fact produced very pronounced background signals. As the length of the toe-hold increased, however, this background dropped to near zero (8 nt and higher; for example, see FIG. 17F), whereas in all cases the THSTS have a fairly consistent and relatively high background translation rate, also referred to as "leak." As toe-hold lengths increased beyond 11 nt, moreover, clashing interactions on THSTs began to dominate the system and slow down foreground activity dramatically, whereas RSTs operate nominally with longer toe-hold rates (see, e.g., FIG. 17I-M).

In another series of simulations, an 8 nt toe-hold at 100 nm translator concentrations produced similar foreground signals for both RSTs and THSTs. The systems were examined with increasing depth of the network, in terms of number of stages, i.e., the number of translators. As shown in FIG. 18A-D, with increasing numbers of stages the background signals of both RSTs and THSTs increased markedly. The degree of this increase was dramatically worse in the case of THSTs, however.

Yet another series of simulations examined moderate sized networks (5 stages), with both long (13 nt) and short (8 nt) toe-holds, and showed how their behavior changed with variation in concentration of the translators. The results are presented in FIG. 19A-N. Higher concentration translations (10 μM) proceeded very rapidly, and very low concentration translations (100 pM) proceeded very slowly. This behavior is consistent with the fact that both the RST and the THST systems employ second order reaction kinetics, hence, time to equilibrium is dependent on the total concentration of the system.

In the case of long toe-holds, reaction timescales remained biologically relevant for RST to far lower concentrations, which were still showing modest reactivity down at 100 pM, whereas THST required much higher concentration (10 μM) to obtain any meaningful activity (FIG. 19A-G). In the case of short toe-holds, RSTs preformed similarly, although with markedly higher background signals (FIG. 19H-N). THSTs with these shorter toe-holds managed to obtain meaningful reactivity at low concentrations, but at high concentrations the leak contributing to background signals of the THSTs were catastrophically high.

Together these data demonstrate that RSTs offer design possibilities whereby background (leak) activity can be reduced to nearly undetectable levels with longer toe-hold, without losing reactivity through extreme inhibition as the THSTs face. Furthermore, they show that RSTs can function with ideal foreground-to-background reactivity in an enormous dynamic range of concentrations, suiting them ideally for use under biological circumstances.

While particular embodiments of the subject invention have been discussed, they are illustrative only and not restrictive of the invention. A review of this specification will make many variations of the invention apparent to those skilled in the field of the invention. The full scope of the invention should be determined by reference both to the claims below, along with their full range of equivalents, and to the specification, with such variations.

What is claimed is:

1. A composition comprising a first, a second and a third nucleic acid complexes, wherein:

the first complex comprises a first, a second, a third and a fourth nucleic acid strands each comprising, sequentially, a first, a second and a third fragments and defined as B-W-D, $\overline{C}$-$\overline{W}$-$\overline{A}$, $\overline{D}$-$\overline{Y}$-H, and $\overline{G}$-Y-C, respectively, wherein each letter denotes a fragment and each string of letters connected by "-" denotes a strand, and wherein the first complex comprises a first duplex region (W::$\overline{W}$) formed between the second fragments of the first and second strands, a second duplex region ($\overline{Y}$::Y) formed between the second fragments of the third and fourth strands, a third duplex region (D::$\overline{D}$) formed between the third fragment of the first strand and the first fragment of the third strand; and a fourth duplex region ($\overline{C}$::C) formed between the first fragment of the second strand and the third fragment of the fourth strand;

the second complex comprises a first, a second, a third and a fourth nucleic acid strands each comprising, sequentially, a first, a second and a third fragments and defined as F-X-H, $\overline{G}$-$\overline{X}$-$\overline{E}$, $\overline{H}$-$\overline{Z}$-$\overline{I}$ and J-Z-G, respectively, wherein the second complex comprises a first duplex region (X::$\overline{X}$) formed between the second fragments of the first and second strands, a second duplex region ($\overline{Z}$::Z) formed between the second fragments of the third and fourth strands, a third duplex region (H::$\overline{H}$) formed between the third fragment of the first strand and the first fragment of the third strand; and a fourth duplex region ($\overline{G}$::G) formed between the first fragment of the second strand and the third fragment of the fourth strand;

the third complex comprises a first, a second, a third, a fourth, a fifth and a sixth nucleic acid strands each comprising, sequentially, a first, a second and a third fragments and defined as $\overline{C}$-$\overline{Y}$-G, $\overline{H}$-Y-D, $\overline{G}$-Z-J, I-Z-H, J-Q-M and $\overline{N}$-$\overline{Q}$-$\overline{I}$, respectively, wherein the third complex comprises a first duplex region ($\overline{Y}$::Y) formed between the second fragments of the first and second strands, a second duplex region ($\overline{Z}$::Z) formed between the second fragments of the third and fourth strands, a third duplex region (Q::$\overline{Q}$) formed between the second fragments of the fifth and sixth strands, a fourth duplex region (G::$\overline{G}$) formed between the third fragment of the first strand and the first fragment of the third strand; a fifth duplex region ($\overline{H}$::H) formed between the first fragment of the second strand and the third fragment of the fourth strand, a sixth duplex region ($\overline{J}$::J) formed between the third fragment of the third strand and the first fragment of the fifth strand, and a seventh duplex region (I::$\overline{I}$) formed between the first fragment of the fourth strand and the third fragment of the sixth strand;

wherein, in the first complex, the first fragment (B) of the first strand, the third fragment ($\overline{A}$) of the second fragment, the third fragment (H) of the third strand, and the first fragment ($\overline{G}$) of the fourth strand are single-stranded; in the second complex, the first fragment (F) of the first strand, the third fragment ($\overline{E}$) of the second fragment, the third fragment ($\overline{I}$) of the third strand, and the first fragment (J) of the fourth strand are single-stranded; and in the third complex, the first fragment ($\overline{C}$) of the first strand, the third (D) fragment of the second strand, the third fragment (M) of the fifth fragment, and the first fragment ($\overline{N}$) of the sixth strand are single-stranded, and wherein:
- the third strand ($\overline{D}$-$\overline{Y}$-H) of the first complex and the second strand ($\overline{H}$-Y-D) of the third complex have sequence complementarity to allow binding therebetween;
- the fourth strand ($\overline{G}$-Y-C) of the first complex and the first strand ($\overline{C}$-Y-G,) of the third complex have sequence complementarity to allow binding therebetween;
- the third strand ($\overline{H}$-$\overline{Z}$-$\overline{I}$) of the second complex and the fourth strand (I-Z-H) of the third complex have sequence complementarity to allow binding therebetween; and
- the fourth strand (J-Z-G) of the second complex and the third strand ($\overline{G}$-$\overline{Z}$-$\hat{J}$) of the third complex have sequence complementarity to allow binding therebetween.

2. The composition of claim 1, wherein each fragment is from about 5 bases to about 50 bases long.

3. The composition of claim 1, wherein each fragment that is single-stranded is from about 5 bases to about 30 bases long.

4. The composition of claim 1, further comprising a pharmaceutically acceptable carrier.

5. A cell comprising the composition of claim 1.

* * * * *